United States Patent
Barberousse et al.

(10) Patent No.: US 8,013,010 B2
(45) Date of Patent: Sep. 6, 2011

(54) 5-THIOXYLOPYRANOSE COMPOUNDS

(75) Inventors: Véronique Barberousse, Hauteville-les-Dijon (FR); Didier Thomas, Saint Apollinaire (FR); Michel Bondoux, Fontaine les Dijon (FR)

(73) Assignee: Laboratoires Fournier S.A., Dijon Cedex (FR)

( * ) Notice: Subject to any disclaimer, the term of this patent is extended or adjusted under 35 U.S.C. 154(b) by 351 days.

(21) Appl. No.: 12/411,765

(22) Filed: Mar. 26, 2009

(65) Prior Publication Data

US 2009/0186840 A1    Jul. 23, 2009

Related U.S. Application Data

(63) Continuation of application No. PCT/FR2007/052006, filed on Sep. 26, 2007.

(30) Foreign Application Priority Data

Sep. 27, 2006    (FR) ..................... 06 53962

(51) Int. Cl.
*A61K 31/382*    (2006.01)
*C07D 335/02*    (2006.01)

(52) U.S. Cl. ........................ 514/432; 549/28
(58) Field of Classification Search ..................... 549/28
See application file for complete search history.

(56) References Cited

U.S. PATENT DOCUMENTS

| | | | |
|---|---|---|---|
| 4,432,973 A | 2/1984 | Picart | |
| 4,877,808 A | 10/1989 | Samreth et al. | |
| 5,100,913 A | 3/1992 | Samreth et al. | |
| 5,101,048 A | 3/1992 | Bajgrowicz et al. | |
| 5,169,838 A | 12/1992 | Samreth et al. | |
| 7,414,072 B2 * | 8/2008 | Sato et al. ..................... | 514/432 |

FOREIGN PATENT DOCUMENTS

| | | |
|---|---|---|
| EP | 0 051 023 A1 | 5/1982 |
| EP | 0 290 321 A1 | 11/1988 |
| EP | 0 365 397 A2 | 4/1990 |
| EP | 0 367 321 A1 | 5/1990 |
| EP | 0 367 671 A2 | 5/1990 |
| EP | 0 421 829 A1 | 4/1991 |
| EP | 0 451 007 A1 | 10/1991 |
| WO | WO 2005/030785 A2 | 4/2005 |

OTHER PUBLICATIONS

International Search Report dated Jan. 24, 2008 with partial English translation (Six (6) pages).
Bellamy F et al: "Thioxyloside Derivatives as Orally Active Venous Antithrombotics", European Journal of Medicinal Chemistry, Editions Scientifique Elsevier, Paris, FR, vol. 30, 1995, pp. 101S-115S, XP002042895, ISSN: 0223-5234.

* cited by examiner

*Primary Examiner* — Andrew D Kosar
*Assistant Examiner* — Karen Cheng
(74) *Attorney, Agent, or Firm* — Crowell & Moring LLP

(57) ABSTRACT

Compounds of 5-thioxylopyranose, preferably derivatives of the 5-thioxilopyranose type, a method for preparing such compounds, and the use of such compounds as an active ingredient in pharmaceutical compositions which are useful, in particular, for treating or inhibiting thrombosis or heart failure or thromboembolic disease states.

12 Claims, No Drawings ns
5-THIOXYLOPYRANOSE COMPOUNDS

CROSS REFERENCE TO RELATED APPLICATIONS

This application is a continuation of international application no. PCT/FR2007/052006, filed Sep. 26, 2007 designating the United States of America, and published in French on Apr. 3, 2008 as WO 2008/0037923, the entire disclosure of which is incorporated herein by reference. Priority is claimed based on French patent application no. FR 0652962, filed Sep. 27, 2006.

FIELD OF THE INVENTION

The present invention relates to novel 5-thioxylose compounds, preferably derivatives of 5-thioxylopyranose type, and to their process of preparation and to their use as active substance of medicaments, intended in particular for the treatment or inhibition of thrombosis.

PRIOR ART

D-Xylose or 5-β-D-thioxylose derivatives are already known, for example in EP051 023B1, EP290321B1, EP365397B1, EP367321B1, EP421 829B1, EP 451 007 B1 and WO 2005/030 785 or in the publications J. Med. Chem. Vol. 36, No. 7, pp 898-903 and Eur. J. Med. Chem., Vol. 30, pp 101S-105S (1995). The compounds described in these documents are of use in reducing the risks of venous thrombosis in man. The mechanism of action of these compounds appears to be an effect on glycosaminoglycans (J. Biol. Chem., Vol. 270, No. 6, pp 2662-68, Thromb. Haemost., 1999, 81, pp 945-950). These compounds have an aglycone part of aromatic structure, such as various substituted benzopyranone, benzophenone, phenyl or pyridine derivatives. The term "aglycone part" is understood to mean the non-glucide part of these compounds.

Furthermore, it is known that the beneficial effects of a transluminal coronary angioplasty can be compromised due to restenosis of the vessel, thus causing a fresh obstruction of the arterial lumen. Compounds which make it possible to avoid this restenosis are thus of the greatest advantage in maintaining a satisfactory diagnosis following the surgical operation with regard to artherosclerosis.

OBJECT OF THE INVENTION

Novel compounds structurally different from the compounds of the prior art and which exhibit a good effectiveness when they are administered orally with an excellent pharmacological result (generally approximately 100%) against the appearance of arterial or venous thrombosis, have now been discovered, and these are the subject matter of the present invention.

DESCRIPTION

The novel compounds according to the invention are characterized in that they are chosen from:

a) the compounds of formula:

I in which:

the pentapyranosyl group represents a 5-thio-β-D-xylopyranosyl group,

R represents a hydrogen atom or a $C_2$-$C_6$ acyl group,

R' and R" each independently represent a hydrogen atom, a halogen atom or a $C_1$-$C_4$ alkyl group, A represents a 5- or 6-membered aromatic ring of formula:

in which:

X represents a nitrogen, oxygen or sulfur atom,

Y represents a carbon atom or a single bond, $Z_1$, $Z_2$ and $Z_3$ each independently represent a carbon or nitrogen atom, $R_1$, $R_2$ and $R_3$ each independently represent a hydrogen atom, a halogen atom, a cyano group, a $C_1$-$C_4$ alkyl group, a hydroxyl group, a $C_1$-$C_4$ alkoxy group, a trifluoromethyl group or a dialkylamino group; or $R_1$ and $R_2$ form, together with the atoms of the heterocycle to which they are attached, an aromatic ring comprising 6 carbon atoms, A thus representing a fused bicyclic group, in particular a benzothiazolyl, benzofuranyl, indolyl or benzothienyl group, b) their addition salts, c) their metabolites.

The invention also relates to the compounds of formula I for their use as pharmacologically active substance.

In particular, the invention relates to the use of at least one substance chosen from the compounds of formula I and their nontoxic salts in the preparation of a medicament, of use in human or animal therapeutics, intended for the inhibition or treatment of thrombosis, in particular venous thrombosis. The compounds according to the invention are also of use as active substances of medicaments intended for the inhibition of restenosis after transluminal coronary angioplasty. As the compounds according to the invention are active according to a method of action involving glycosaminoglycans, they may also be of use as active substance of a medicament intended for the treatment or inhibition of any other disease in which glycosaminoglycans are involved.

DETAILED DESCRIPTION

In the formula I, the term "$C_1$-$C_4$ alkyl group" is understood to mean a saturated, linear or branched, hydrocarbon chain having from 1 to 4 carbon atoms or one which is partially or completely cyclized, the cyclized portion having 3 or 4 carbon atoms. Examples of $C_1$-$C_4$ alkyl groups are in particular the methyl, ethyl, propyl, butyl, 1-methylethyl, 1,1-dimethylethyl, 1-methylpropyl, 2-methylpropyl, cyclopropyl or cyclo-propylmethyl groups.

The term "halogen" should be understood as meaning a fluorine, chlorine, bromine or iodine atom and preferably a fluorine or chlorine atom.

The term "$C_2$-$C_6$ acyl group" is understood to mean an R—CO— group in which R represents an alkyl group as defined above having from 1 to 5 carbon atoms. Examples of $C_2$-$C_6$ acyl groups are in particular the acetyl, propanoyl, butanoyl, pentanoyl or hexanoyl groups and their homologs in which the chain can be branched.

The term "$C_1$-$C_4$ alkoxy group" is understood to mean an RO— group in which R represents an alkyl group having from 1 to 4 carbon atoms as defined above. Mention may be made, as examples of $C_1$-$C_4$ alkoxy groups, of the methoxy, ethoxy, propoxy, butoxy, 1-methylethoxy, 1,1-dimethylethoxy, 1-methylpropoxy, 2-methylpropoxy or cyclopropylmethoxy groups.

The term "dialkylamino group" is understood to mean an —NRR" group in which R and R" independently represent a $C_1$-$C_4$ alkyl group as defined above.

The term "addition salts" is understood to mean the addition salts obtained by reaction of a compound of formula I with an inorganic or organic acid. Preferably, the addition salts are pharmaceutically acceptable addition salts. The hydrates or solvates of the compounds of formula I or of the salts of the compounds of formula I also form an integral part of the invention.

Preference is given, among the inorganic acids suitable for salifying a basic compound of formula I, to hydrochloric, hydrobromic, phosphoric and sulfuric acids. Preference is given, among the organic acids suitable for salifying a basic compound of formula I, to methanesulfonic, benzenesulfonic, toluenesulfonic, maleic, fumaric, oxalic, citric, tartaric, lactic and trifluoroacetic acids.

The term "active metabolites" is understood to mean the compounds which are produced in the biological medium from the compounds of formula I and which have a pharmacological activity of the same nature as the compounds of formula I which are described in the present patent application. By way of example, the compounds of formula I can be metabolized as the result of a hydroxylation reaction to provide a novel compound (metabolite) which retains a pharmacological activity of the same nature as that of the compounds of formula I.

As specific examples of fused bicyclic groups represented by A in the case where $R_1$ and $R_2$ together form an aromatic ring comprising 6 carbon atoms, mention may be made of the benzofuranyl, benzothienyl, benzisoxazolyl, benzoxazolyl, benzimidazolyl, quinolinyl, quinoxalinyl, quinazolinyl, indolyl, benzothiazolyl or indazolyl groups.

Among the compounds according to the present invention, preference is very particularly given to those in which A represents a pyridinyl ring.

Among the compounds according to the present invention, preference is also given to the compounds in which R is the hydrogen atom or the —COCH$_3$ group.

Compounds which are particularly preferred according to the present invention are the compounds of formula I in which the pyridinyl ring and the thioxylose group are in the meta relative position on the benzene ring.

Other preferred compounds in the context of the present invention are the compounds of abovementioned formula I in which the pyridinyl ring and the thioxylose group are in the para relative position on the benzene ring.

The compounds of formula I according to the invention can be prepared by employing the glycosylation methods known to a person skilled in the art, in particular:

a) the Helferich method described in the work "The Carbohydrate, Chemistry and Biochemistry", $2^{nd}$ edition, Academic Press, New York-London, 1972, Volume IA, pages 292-294, by condensation of a peracetylated sugar with a phenol derivative in the presence of a Lewis acid;

b) the Koenigs-Knorr method (idem, pages 295-299), by condensation of a halogenated acylose with a hydroxyl group having a phenolic nature in the presence of a proton acceptor, such as mercuric cyanide, silver imidazolate or silver trifluoromethanesulfonate;

c) the Schmidt method, by condensation of an osyl trichloroacetimidate with a phenol derivative in the presence of a Lewis acid, such as, for example, trimethylsilyl trifluoromethanesulfonate or boron trifluoride etherate.

The compounds of formula I are preferably prepared according to methods derived from the abovementioned processes.

According to a first general process, the following steps are carried out:

a) reacting a phenol of formula:

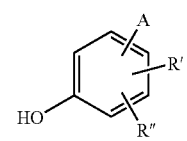

II in which:

R' and R" each independently represent a hydrogen atom, a halogen atom or a $C_1$-$C_4$ alkyl group, A represents a 5- or 6-membered aromatic ring of formula:

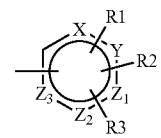

in which:

X represents a nitrogen, oxygen or sulfur atom,

Y represents a carbon atom or a single bond, $Z_1$, $Z_2$ and $Z_3$ each independently represent a carbon or nitrogen atom, $R_1$, $R_2$ and $R_3$ each independently represent a hydrogen atom, a halogen atom, a cyano group, a $C_1$-$C_4$ alkyl group, a hydroxyl group, a $C_1$-$C_4$ alkoxy group, a trifluoromethyl group or a dialkylamino group; or $R_1$ and $R_2$ form, together with the atoms of the heterocycle to which they are attached, an aromatic ring comprising 6 carbon atoms, A thus representing a fused bicyclic group, in particular a benzothiazolyl, benzofuranyl, indolyl or benzothienyl group,
with a 5-thioxylopyranose derivative of formula:

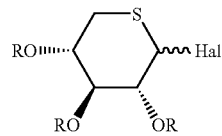

in which Hal represents a halogen, preferably bromine, and R represents a $C_2$-$C_6$ acyl group, preferably the acetyl group, in an aprotic solvent, such as acetonitrile or toluene, in the presence of a silver salt, in particular silver oxide or imidazolate, or of a zinc salt (in particular the oxide or the chloride), in an anhydrous medium, at a temperature of between 25 and 110° C. and for 1 to 10 hours, in order to obtain the compound of formula:

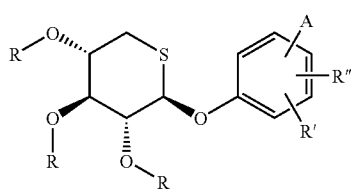

in which A, R', R' and R" retain the same meanings as in the starting compounds;

b) if necessary, reacting the compound of formula I obtained above with a solution of ammonia in methanol in order to bring about the deacylation and thus to replace the acyl group by hydrogen atoms and to obtain the compound of formula:

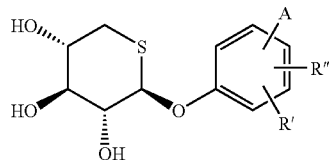

in which $R_1$ and $R_2$ retain the same meanings as above;

c) if necessary, reacting one of the compounds I or Ia obtained above with an acid according to methods known to a person skilled in the art in order to obtain the corresponding addition salt.

In an alternative form of stage b) described above, the replacement of the acyl group by a hydrogen atom can be brought about by the action of a metal alkoxide, preferably sodium methoxide in a catalytic amount in methanol, at a temperature of between 0 and 30° C. and for 0.5 to 2 hours, in order to obtain the compound of formula Ia from the compound of formula I in which R represents a $C_2$-$C_6$ acyl group.

According to a second process, the compounds of formula I can be obtained by reaction of tetra-O-acetyl-5-thioxylopyranose of formula:

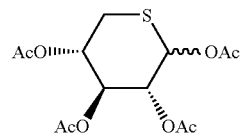

in which Ac represents the acetyl group, with a phenol of formula:

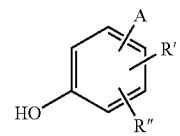

in which:
R' and R" each independently represent a hydrogen atom, a halogen atom or a $C_1$-$C_4$ alkyl group,
A represents a 5- or 6-membered aromatic ring of formula:

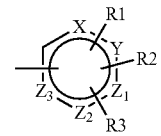

in which:
X represents a nitrogen, oxygen or sulfur atom,
Y represents a carbon atom or a single bond,
$Z_1$, $Z_2$ and $Z_3$ each independently represent a carbon or nitrogen atom,
$R_1$, $R_2$ and $R_3$ each independently represent a hydrogen atom, a halogen atom, a cyano group, a $C_1$-$C_4$ alkyl group, a hydroxyl group, a $C_1$-$C_4$ alkoxy group, a trifluoromethyl group or a dialkylamino group; or
$R_1$ and $R_2$ form, together with the atoms of the heterocycle to which they are attached, an aromatic ring comprising 6 carbon atoms, A thus representing a fused bicyclic group, in particular a benzothiazolyl, benzofuranyl, indolyl or benzothienyl group,
in an aprotic solvent, such as, for example, dichloromethane, in the presence of a catalyst of Lewis acid type, for example tin tetrachloride, at a temperature of between 20 and 60° C. and for 1 to 2 hours, in order to obtain the compound of formula:

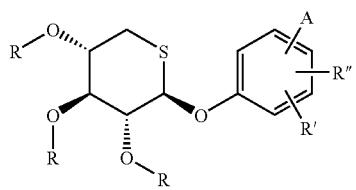

in which A, R, R' and R" retain the same meanings as in the starting compounds.

The compound of formula I can subsequently be reacted according to the protocol described in the preceding process in order to obtain the unsubstituted pyranosyl compound (Ia) and/or a salt with an acid.

According to a third process, the compounds of formula I can be obtained by reacting a thioxylose derivative of formula:

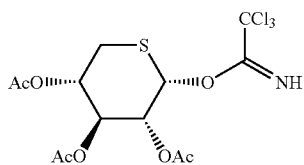

in which Ac represents the acetyl group,
with a phenol of formula:

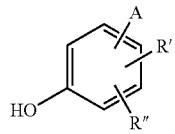

II in which:

R' and R" each independently represent a hydrogen atom, a halogen atom or a $C_1$-$C_4$ alkyl group, A represents a 5- or 6-membered aromatic ring of formula:

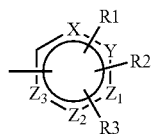

in which:

X represents a nitrogen, oxygen or sulfur atom,

Y represents a carbon atom or a single bond, $Z_1$, $Z_2$ and $Z_3$ each independently represent a carbon or nitrogen atom, $R_1$, $R_2$ and $R_3$ each independently represent a hydrogen atom, a halogen atom, a cyano group, a $C_1$-$C_4$ alkyl group, a hydroxyl group, a $C_1$-$C_4$ alkoxy group, a trifluoromethyl group or a dialkylamino group; or $R_1$ and $R_2$ form, together with the atoms of the heterocycle to which they are attached, an aromatic ring comprising 6 carbon atoms, A thus representing a fused bicyclic group, in particular a benzothiazolyl, benzofuranyl, indolyl or benzothienyl group, in an aprotic solvent, such as dichloromethane, in the presence of a catalyst, such as trimethylsilyl trifluoromethanesulfonate, at a temperature of between −25° C. and ambient temperature and for 1 to 5 hours, in order to obtain the thioxylopyranoside of formula:

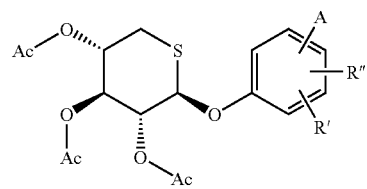

Ib in which A, R' and R" retain the same meanings as in the starting compounds.

The compound of formula Ib thus obtained can subsequently be reacted as above in order to obtain the unsubstituted pyranosyl compounds and/or the acid salts.

The compounds of formula I according to the invention can also advantageously be prepared from halogenated derivatives of a glycosylated benzene ring by a Suzuki-type coupling reaction between two aromatic and heteroaromatic rings.

According to a general process, the following steps are carried out:

a) reacting a compound of formula:

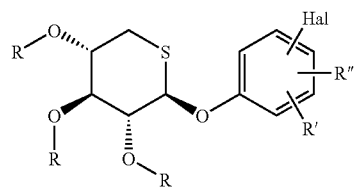

in which Hal is a halogen atom, preferably bromine or iodine, R' and R" each independently represent a hydrogen atom, a halogen atom (other than bromine or iodine) or a $C_1$-$C_4$ alkyl group, and R represents a hydrogen atom or a $C_2$-$C_6$ acyl group;

with a heteroarylboronic acid or an alkyl heteroarylboronate of formula:

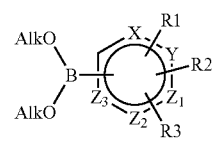

in which:

X represents a nitrogen, oxygen or sulfur atom,

Y represents a carbon atom or a single bond, $Z_1$, $Z_2$ and $Z_3$ each independently represent a carbon or nitrogen atom, $R_1$, $R_2$ and $R_3$ each independently represent a hydrogen atom, a halogen atom, a cyano group, a $C_1$-$C_4$ alkyl group, a hydroxyl group, a $C_1$-$C_4$ alkoxy group, a trifluoromethyl group or a dialkylamino group; or $R_1$ and $R_2$ form, together with the atoms of the heterocycle to which they are attached, an aromatic ring comprising 6 carbon atoms, Alk represents a hydrogen atom or a $C_1$-$C_4$ alkyl group, it additionally being possible for the combination

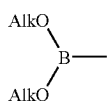

to represent a "4,4,5,5-tetramethyl-1,3,2-dioxaborolan-2-yl" group, abbreviated in the continuation of the text to "pinacolatoboryl"

in the presence of a palladium catalyst, such as the [1,1'-bis(diphenyl-phosphino)ferrocene]dichloropalladium complex with dichloromethane, a palladium catalyst immobilized on resin or Herrmann's catalyst, of a polar solvent, such as methanol, and of cesium fluoride or sodium carbonate or other inorganic bases, optionally with the addition of lithium chloride, at a temperature of between 70° C. and 150° C. for 5 minutes to 72 hours using microwave radiation or a conventional heating method, in order to obtain the compound of formula:

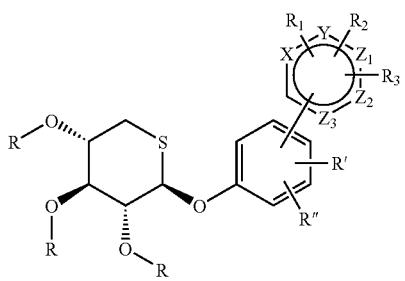

in which:
<
R, $R_1$, $R_2$, $R_3$, R', R", X, Y, $Z_1$, $Z_2$ and $Z_3$ retain the same meanings as in the starting materials;

b) if necessary, reacting the compound of formula I obtained above with a solution of ammonia in methanol in order to bring about the deacylation and thus to replace the acyl group by hydrogen atoms and to obtain the compound of formula:

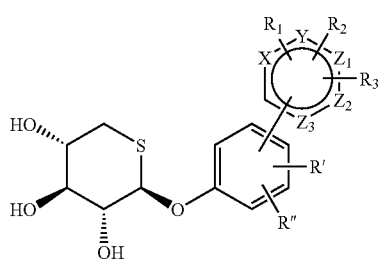

Ia in which $R_1$, $R_2$, $R_3$, R', R", X, Y, $Z_1$, $Z_2$ and $Z_3$ retain the same meanings as above;

c) if necessary, reacting one of the compounds I or Ia obtained above with an acid according to methods known to a person skilled in the art in order to obtain the corresponding addition salt.

For compounds of this type, another similar process consists in reacting a glycosylated phenylboronic acid or a glycosylated phenylboronate of formula:

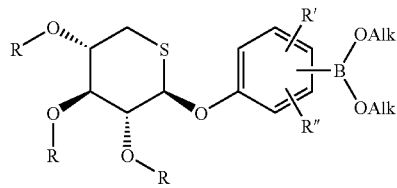

in which R represents a hydrogen atom or a $C_2$-$C_6$ acyl group, R' and R" each independently represent a hydrogen atom, a halogen atom (other than bromine or iodine) or a $C_1$-$C_4$ alkyl group, and
Alk represents a hydrogen atom or a $C_1$-$C_4$ alkyl group; it additionally being possible for the combination

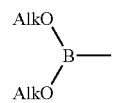

to represent a "pinacolatoboryl" group,
with a heteroaryl halide of formula:

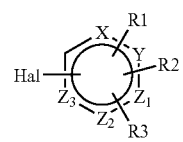

in which Hal represents a halogen, preferably bromine or iodine, and
$R_1$, $R_2$ and $R_3$ each independently represent a hydrogen atom, a halogen atom, a cyano group, a $C_1$-$C_4$ alkyl group, a hydroxyl group, a $C_1$-$C_4$ alkoxy group, a trifluoromethyl group or a dialkylamino group; or
$R_1$ and $R_2$ form, together with the atoms of the heterocycle to which they are attached, an aromatic ring comprising 6 carbon atoms,
under the same conditions as above, in order to obtain the compound of formula:

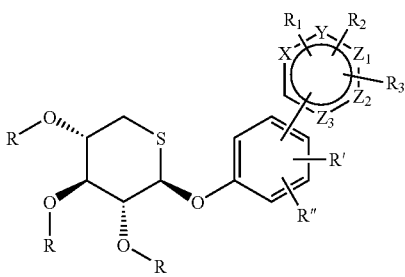

in which:
R, $R_1$, $R_2$, $R_3$, R', R", X, Y, $Z_1$, $Z_2$ and $Z_3$ retain the same meanings as in the starting materials.

Generally, it is preferable to use 2,3,4-tri-O-acetyl-5-thio-α-D-xylopyranosyl bromide or tetra-O-acetyl-5-thio-α-D-xylopyranose when it is a matter of obtaining a β-D-5-thioxylopyranose derivative.

The compounds of aryl- or heteroarylboronic type are known or novel compounds and can be prepared according to processes known to a person skilled in the art, starting from halogenated aromatic or heteroaromatic derivatives, by reaction with, for example, bis(pinacolato)diboron, if it is desired to obtain a boronic ester, by replacement of the halogen atom.

The glycosylation reactions described above generally result in a mixture of the isomers of α and β configuration and it is generally necessary to optimize the operating conditions in order to obtain proportions favorable to the isomer of β configuration. For this same reason, it may also be necessary to carry out purifications, either by recrystallization or by chromatography, in order to obtain the pure β isomer.

The general processes for the synthesis of the compounds according to the invention are described with the use of conventional heating methods (oil bath, heating mantle, jacket, and the like). These heating methods can be replaced by heating by microwave radiation. In this case, the temperature maintenance times are greatly reduced.

The aim of the following examples is to illustrate the invention and they should under no circumstances limit the scope thereof. The melting points are measured on a Kofler bench.

The following abbreviations have been used:
mmol (or mM) means millimole ($10^{-3}$ mol)
DMSO denotes dimethyl sulfoxide
THF denotes tetrahydrofuran
$CHCl_3$ denotes chloroform
$CH_3OH$ denotes methanol
The "pinacolatoboryl" group means:

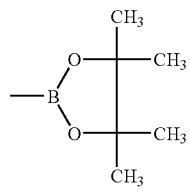

Preparation I

3-Iodophenyl 2,3,4-tri-O-acetyl-5-thio-β-D-xylopyranoside 38.63 g (0.28 mol) of zinc chloride are heated until molten under an argon atmosphere in a reactor. After cooling the reaction mass, 800 ml of toluene, 800 ml of acetonitrile and 44 g of 4 Å molecular sieve are added. The reaction mixture is stirred at ambient temperature for 90 minutes and 25 g (0.113 mol) of 3-iodophenol are added. The reaction mixture is brought to 90° C. and, after 2 minutes, 39 ml (0.28 mol) of triethylamine and 44.39 g (0.12 mol) of 2,3,4-tri-O-acetyl-5-thio-α-D-xylopyranosyl bromide are added. The reaction mixture is kept stirred at 80° C. for 30 minutes. After cooling, water and ethyl acetate are added and the insoluble compounds are removed by filtration. The organic phase is washed successively with water, a 1N sodium hydroxide solution and a saturated sodium chloride solution. The organic phase is dried over magnesium sulfate, decolored using active charcoal, filtered and evaporated under reduced pressure. The residue is purified by chromatography on a silica column, elution being carried out using a cyclohexane/ethyl acetate mixture (70/30; v/v), and recrystallized from isopropanol. The expected product is obtained in the form of a white powder with a yield of 37%.

M.p.=127° C.
$[\alpha]_D^{29}=-11°$ (c=0.43; DMSO).

By carrying out the operation analogously to preparation I, starting from the appropriate halogenated phenols, the following intermediates are obtained:

Preparation II

4-Iodophenyl 2,3,4-tri-O-acetyl-5-thio-β-D-xylopyranoside white powder (yield=32%).
M.p.=148° C.
$[\alpha]_D^{29}=-7°$ C. (c=0.35; DMSO).

Preparation III

4-Bromo-3,5-dimethylphenyl 2,3,4-tri-O-acetyl-5-thio-β-D-xylopyranoside pink powder (yield=25%).
M.p.=159° C.
$[\alpha]_D^{30}=9.2°$ (c=0.1; DMSO).

Preparation IV

2-Bromophenyl 2,3,4-tri-O-acetyl-5-thio-β-D-xylopyranoside white powder (yield=33%).
M.p.=176° C.
$[\alpha]_D^{29}=-242°$ (c=0.2; $CH_3OH$).

Preparation V

2-Bromo-5-fluorophenyl 2,3,4-tri-O-acetyl-5-thio-β-D-xylopyranoside white solid (yield=61%).
M.p.=174° C.
$[\alpha]_D^{26}=-109°$ (c=0.18; DMSO).

Preparation VI

4-Bromo-2-fluorophenyl 2,3,4-tri-O-acetyl-5-thio-β-D-xylopyranoside white solid (yield=46%).
M.p.=131° C.
$[\alpha]_D^{29}=-27°$ (c=0.27; DMSO).

Preparation VII

3-Bromophenyl 2,3,4-tri-O-acetyl-5-thio-β-D-xylopyranoside white solid (yield=32%).
M.p.=157° C.
$[\alpha]_D^{32}=-21°$ (c=0.44; DMSO).

Preparation VIII

5-Bromo-2,3-difluorophenyl 2,3,4-tri-O-acetyl-5-thio-β-D-xylopyranoside cream powder (yield=73%).
M.p.=135° C.
$[\alpha]_D^{25}=-62°$ (c=0.36; CHCl$_3$).

Preparation IX

3-Bromo-4-chlorophenyl 2,3,4-tri-O-acetyl-5-thio-β-D-xylopyranoside white powder (yield=37%).
M.p.=177° C. (crystallized from ethyl ether).
$[\alpha]_D^{27}=-7°$ (c=0.16; DMSO).

Preparation X

5-Bromo-2-chlorophenyl 2,3,4-tri-O-acetyl-5-thio-β-D-xylopyranoside white powder (yield=35%).
M.p.=250° C. (crystallized from ethyl ether).
$[\alpha]_D^{30}=-27°$ (c=0.21; DMSO).

Preparation XI

5-Bromo-2-fluorophenyl 2,3,4-tri-O-acetyl-5-thio-β-D-xylopyranoside white solid (yield=56%).
M.p.=122° C.
$[\alpha]_D^{35}=43°$ (c=0.40; DMSO).

Preparation XII

5-Bromo-2-pyridinyl Acetate

A suspension of 0.5 g (2.87 mmol) of 5-bromo-2-pyridinol in 10 ml of ethyl ether is prepared and 1 ml (7.1 mmol) of triethylamine and then 1 ml (14 mmol) of acetyl chloride are added at ambient temperature. The mixture is stirred at ambient temperature for 24 hours and the insoluble materials are removed by filtration. The filtrate is concentrated under reduced pressure and the crude product is purified by chromatography on silica gel, elution being carried out using a toluene/2-propanol mixture (9/1; v/v). The expected product is obtained in the form of a pale yellow powder with a yield of 52%.
$^1$H NMR (DMSO; 300 MHz) δ: 8.52 (d, 1H); 8.19 (dd, 1H); 7.23 (d, 1H); 2.30 (s, 3H).

Example 1

3-(4-Pyridinyl)phenyl 2,3,4-tri-O-acetyl-5-thio-β-D-xylopyranoside 0.4 g (0.809 mmol) of 3-iodophenyl 2,3,4-tri-O-acetyl-5-thio-β-D-xylopyranoside, obtained according to preparation I, is placed under an argon atmosphere in a 10 ml microwave reactor equipped with a magnetic bar. 3.8 ml (1.01 mmol) of 4-pyridineboronic acid, in solution in 6 ml of dimethoxyethane, are added, followed by a 2M potassium carbonate solution (2.18 mmol). Finally, 62 mg (0.08 mmol) of trans-di(μ-acetato)bis[2-(di-o-tolylphosphino)benzyl]dipalladium (II) are added and the reactor is crimped. The reaction mixture is heated at 112° C. for 1 hour using microwave radiation and then filtered. The residual solid is washed with methanol and the combined filtrates are concentrated under reduced pressure. The evaporation residue is taken up in ethyl acetate and washed with a saturated ammonium chloride solution. After drying over magnesium sulfate, the organic phase is concentrated under reduced pressure. The product obtained is purified by chromatography on a silica column, elution being carried out using a dichloromethane/ethyl acetate mixture (15/85 to 20/80; v/v). The expected product is obtained in the form of a yellow powder with a yield of 91%.
M.p.=112° C.
$[\alpha]_D^{27}=-72°$ (c=0.42; CHCl$_3$).

Example 2

3-(4-Pyridinyl)phenyl-5-thio-β-D-xylopyranoside 0.435 g (1.04 mmol) of the product obtained according to example 1 is dissolved in 8 ml of THF, and 5.5 ml of water and 307 mg (7.28 mmol) of lithium hydroxide are added. The reaction mixture is stirred for 2 hours at 44° C. The THF is evaporated under reduced pressure and the evaporation residue is taken up in water and neutralized by addition of 1N hydrochloric acid to neutral pH. A precipitate is formed, which precipitate is isolated by filtration and dried in an oven under vacuum. The expected product is obtained in the form of a light brown powder with a yield of 96%.
M.p.=253° C.
$[\alpha]_D^{28}=-79°$ (c=0.31; DMSO).

Example 3

5-Fluoro-2-(3-pyridinyl)phenyl 2,3,4-tri-O-acetyl-5-thio-β-D-xylopyranoside

A solution of 0.930 g (2 mmol) of 2-bromo-5-fluorophenyl 2,3,4-tri-O-acetyl-5-thio-β-D-xylopyranoside, obtained according to preparation V, in 8 ml of dimethoxyethane is placed in a sealed reactor suitable for microwave radiation and a solution of 0.318 g (3 mmol) of sodium carbonate in 2 ml of water, 0.163 g (0.2 mmol) of the [1,1'-bis-(diphenylphosphino)ferrocene]dichloropalladium(II) complex with dichloromethane and 0.492 g (4 mmol) of 3-pyridineboronic acid are added. The reaction mixture is heated at 110° C. for 20 minutes using microwave radiation and cooled, water is added and extraction is carried out with ethyl acetate. The organic phase is washed with a 0.5M sodium carbonate solution and then with water to neutral pH, dried over magnesium sulfate and concentrated under reduced pressure. The residue obtained is purified by chromatography on a silica column, elution being carried out using a dichloromethane/ethyl acetate mixture (97/3; v/v). The expected product is obtained in the form of a white solid with a yield of 88%.
M.p.=66° C.
$[\alpha]_D^{30}=-65°$ (c=0.24; DMSO).

Example 4

5-Fluoro-2-(3-pyridinyl)phenyl-5-thio-β-D-xylopyranoside 0.4 g (0.86 mmol) of the product obtained according to example 3 is stirred at ambient temperature for 3 hours with 10 ml of a 7M solution of ammonia in methanol. The reaction mixture is concentrated under reduced pressure and the solid product obtained is recrystallized from a CH$_3$OH/H$_2$O mixture (90/10; v/v). The expected product is obtained in the form of a white solid with a yield of 91%.
M.p.=110° C.
$[\alpha]_D^{31}=-69°$ (c=0.19; DMSO).

Example 5

4-(3-Pyridinyl)phenyl 2,3,4-tri-O-acetyl-5-thio-β-D-xylopyranoside

By carrying out the operation analogously to example 1, starting from 4-iodophenyl 2,3,4-tri-O-acetyl-5-thio-β-D-xylopyranoside, obtained according to preparation II, and 3-pyridineboronic acid, the expected product is obtained in the form of a yellow solid with a yield of 79%.
M.p.=150° C.
$[\alpha]_D^{28}=-47°$ (c=0.45; CHCl$_3$).

Example 6

4-(3-Pyridinyl)phenyl 5-thio-β-D-xylopyranoside

By carrying out the operation analogously to example 2, starting from the product obtained according to example 5,4-(3-pyridinyl)phenyl 5-thio-β-D-xylopyranoside is obtained in the form of a light yellow powder with a yield of 83%.
M.p.=166° C.
$[\alpha]_D^{29}=-240°$ (c=0.37; DMSO).

Example 7

4-(4-Pyridinyl)phenyl 2,3,4-tri-O-acetyl-5-thio-β-D-xylopyranoside

By carrying out the operation analogously to example 3, starting from 4-iodophenyl 2,3,4-tri-O-acetyl-5-thio-β-D-xylopyranoside, obtained according to preparation II, and 4-pyridineboronic acid, the expected product is obtained in the form of a cream powder with a yield of 78%.
M.p.=180° C.
$[\alpha]_{27}=-46°$ (c=0.39; CHCl$_3$).

Example 8

4-(4-Pyridinyl)phenyl-5-thio-β-D-xylopyranoside

By carrying out the operation analogously to example 2, starting from the product obtained according to example 7,4-(4-pyridinyl)phenyl 5-thio-β-D-xylopyranoside is obtained in the form of a light brown powder with a yield of 89%.
M.p.=217° C.
$[\alpha]_D^{28}=-44°$ (c=0.28; DMSO).

Example 9

4-(2-Pyridinyl)phenyl 2,3,4-tri-O-acetyl-5-thio-β-D-xylopyranoside 0.499 g (0.101 mmol) of 4-iodophenyl 2,3,4-tri-O-acetyl-5-thio-β-D-xylopyranoside, obtained according to preparation II, is placed, under anhydrous conditions and under argon atmosphere, in a 20 ml microwave reactor equipped with a magnetic bar. 0.542 g (2.02 mmol) of N-phenyldiethanolamine 2-pyridylboronate, in solution in 12.5 ml of dimethoxyethane, is added, followed by 1.38 ml of a 2M potassium carbonate solution (2.76 mmol). Finally, 77 mg (0.41 mmol) of cuprous iodide and 83 mg (0.101 mmol) of the [1,1'-bis(diphenylphosphino)ferrocene]dichloropalladium(II) complex with dichloromethane are added and the reactor is crimped. The reaction mixture is heated at 112° C. for 1 hour in a microwave oven. The cooled reaction mixture is diluted with water and ethyl acetate. The organic phase is separated, then filtered and concentrated under reduced pressure. The product obtained is taken up in ethyl acetate and then washed with an ammonium chloride solution to neutral pH. The organic phase is subsequently dried over sodium sulfate and evaporated under reduced pressure. The residue obtained is purified by chromatography on a silica column, elution being carried out using a dichloromethane/ethyl acetate mixture (0/100 to 6/94; v/v). The expected product is obtained in the form of a white powder with a yield of 49%.
M.p.=125-130° C.
$[\alpha]_D^{26}=-62°$ (c=0.24; CH$_3$OH).

Example 10

4-(2-Pyridinyl)phenyl 5-thio-β-D-xylopyranoside

By carrying out the operation analogously to example 2, starting from the product obtained according to example 9,4-(2-pyridinyl)phenyl 5-thio-β-D-xylopyranoside is obtained in the form of a pale yellow powder with a yield of 97%.
M.p.=197° C.
$[\alpha]_D^{27}=-55°$ (c=0.24; DMSO).

Example 11

3-(2-Pyridinyl)phenyl 2,3,4-tri-O-acetyl-5-thio-β-D-xylopyranoside

By carrying out the operation analogously to example 9, starting from 3-iodophenyl 2,3,4-tri-O-acetyl-5-thio-β-D-xylopyranoside, obtained according to preparation I, the expected product is obtained in the form of white flakes with a yield of 60%.
M.p.=68-97° C.
$[\alpha]_D^{27}=-46°$ (c=0.24; CH$_3$OH).

Example 12

3-(2-Pyridinyl)phenyl 5-thio-β-D-xylopyranoside

By carrying out the operation analogously to example 2, starting from the product obtained according to example 11, 3-(2-pyridinyl)phenyl 5-thio-β-D-xylopyranoside is obtained in the form of a yellow powder with a yield of 79%.
M.p.=138-139° C.
$[\alpha]_D^{27}=-88°$ (c=0.3; DMSO).

Example 13

3,5-Dimethyl-4-(4-pyridinyl)phenyl 2,3,4-tri-O-acetyl-5-thio-β-D-xylopyranoside 1 g (2.1 mmol) of 4-bromo-3,5-dimethylphenyl 2,3,4-tri-O-acetyl-5-thio-β-D-xylopyranoside, obtained according to preparation III, is mixed with 0.310 g (2.52 mmol) of 4-pyridineboronic acid in a 10 ml microwave reactor and then 1.6 g (4.8 mmol) of MP-Carbonate resin (3.03 mmol/g grafted resin from Argonaut) and 0.182 g (0.22 mmol) of the [1,1'-bis(diphenylphosphino)ferrocene]dichloropalladium(II) complex with dichloromethane are added. A dimethoxyethane/methanol mixture (7 ml/3 ml) is added and the reaction mixture is brought to 120° C. for 30 minutes in a microwave oven. After cooling, the reaction medium is filtered and the filtrate is rinsed with methanol and then concentrated under reduced pressure. The residue obtained is purified by chromatography on a silica column, elution being carried out using a toluene/isopropanol mixture (9/1; v/v), and then crystallized from isopropyl ether. The expected product is obtained in the form of an off-white powder with a yield of 31%.

M.p.=170-171° C.

$[\alpha]_D^{30}$=−21° (c=0.2; DMSO).

Example 14

3,5-Dimethyl-4-(4-pyridinyl)phenyl 5-thio-β-D-xylopyranoside

A suspension of 0.3 g (0.6 mmol) of the product obtained according to example 13 in 10 ml of methanol is formed. 0.3 ml (1.04 mmol) of a solution of sodium methoxide in methanol (3.47 mol/l) is added and the reaction mixture is stirred at ambient temperature for 2 hours. The product in suspension dissolves and then a precipitate is formed and is filtered off. The solid obtained is dried under reduced pressure at 70° C. for 3 hours. The expected product is obtained in the form of a white powder with a yield of 28%.

M.p.=106-107° C.

$[\alpha]_D^{30}$=−54° (c=0.16; DMSO).

Example 15

2-(4-Pyridinyl)phenyl 2,3,4-tri-O-acetyl-5-thio-β-D-xylopyranoside

By carrying out the operation analogously to example 1, starting from 2-bromophenyl 2,3,4-tri-O-acetyl-5-thio-β-D-xylopyranoside, obtained according to preparation IV, and 4-pyridineboronic acid, the expected product is obtained in the form of a white powder with a yield of 65%.

M.p.=165° C.

$[\alpha]_D^{29}$=−108° (c=0.25; CH$_3$OH).

Example 16

2-(4-Pyridinyl)phenyl 5-thio-β-D-xylopyranoside

By carrying out the operation analogously to example 2, starting from the product obtained according to example 15, 2-(4-pyridinyl)phenyl 5-thio-β-D-xylopyranoside is obtained in the form of a white powder with a yield of 52%.

M.p.=134° C.

$[\alpha]_D^{29}$=−138° (c=0.1; CH$_3$OH).

Example 17

2-(3-Pyridinyl)phenyl 2,3,4-tri-O-acetyl-5-thio-β-D-xylopyranoside

By carrying out the operation analogously to example 1, starting from 2-bromophenyl 2,3,4-tri-O-acetyl-5-thio-β-D-xylopyranoside, obtained according to preparation IV, and 3-pyridineboronic acid, the expected compound is obtained. The latter was not isolated and is used directly in the following stage.

Example 18

2-(3-Pyridinyl)phenyl 5-thio-β-D-xylopyranoside

By carrying out the operation analogously to example 2, starting from the product obtained according to example 17, 2-(3-pyridinyl)phenyl 5-thio-β-D-xylopyranoside is obtained in the form of a white powder with an overall yield (example 17 and example 18) of 27%.

M.p.=195° C.

$[\alpha]_D^{28}$=−168° (c=0.1; CH$_3$OH).

Example 19

3,5-Dimethyl-4-(3-pyridinyl)phenyl 2,3,4-tri-O-acetyl-5-thio-β-D-xylopyranoside

By carrying out the operation analogously to example 13, starting from 4-bromo-3,5-dimethylphenyl 2,3,4-tri-O-acetyl-5-thio-β-D-xylopyranoside, obtained according to preparation III, and 3-pyridineboronic acid, the expected product is obtained in the form of a colorless foam with a yield of 45%.

M.p.=75-80° C.

$[\alpha]_D^{30}$=−1° (c=0.22; DMSO).

Example 20

3,5-Dimethyl-4-(3-pyridinyl)phenyl 5-thio-β-D-xylopyranoside

By carrying out the operation analogously to example 14, starting from the product obtained according to example 19, the expected product is obtained in the form of a brown solid with a yield of 73%.

M.p.=215° C.

$[\alpha]_D^{30}$=−44° (c=0.21; DMSO).

Example 21

3-(3-Pyridinyl)phenyl 2,3,4-tri-O-acetyl-5-thio-β-D-xylopyranoside

By carrying out the operation analogously to example 3, starting from 3-iodophenyl 2,3,4-tri-O-acetyl-5-thio-β-D-xylopyranoside, obtained according to preparation I, and 3-pyridineboronic acid, the expected product is obtained in the form of a light brown powder with a yield of 66%.

M.p.=123-126° C.

$[\alpha]_D^{27}$=−68° (c=0.4; CHCl$_3$).

Example 22

3-(3-Pyridinyl)phenyl 5-thio-β-D-xylopyranoside

By carrying out the operation analogously to example 2, starting from the product obtained according to example 21, 3-(3-pyridinyl)phenyl 5-thio-β-D-xylopyranoside is obtained in the form of a cream powder with a yield of 99%.

M.p.=197° C.

$[\alpha]_D^{28}$=−84° (c=0.29; DMSO).

Example 23

2-Fluoro-4-(3-pyridinyl)phenyl 2,3,4-tri-O-acetyl-5-thio-β-D-xylopyranoside By carrying out the operation analogously to example 3, starting from 4-bromo-2-fluorophenyl 2,3,4-tri-O-acetyl-5-thio-β-D-xylopyranoside, obtained according to preparation VI, and 3-pyridineboronic acid, the expected product is obtained in the form of a white solid with a yield of 61%.
M.p.=122° C.
$[\alpha]_D^{28=8°}$ (c=0.36; DMSO).

Example 24

2-Fluoro-4-(3-pyridinyl)phenyl 5-thio-β-D-xylopyranoside

By carrying out the operation analogously to example 4, starting from the product obtained according to example 23, 2-fluoro-4-(3-pyridinyl)phenyl 5-thio-β-D-xylopyranoside is obtained in the form of a white solid with a yield of 73%.
M.p.=207° C.
$[\alpha]_D^{28}=-27°$ (c=0.43; DMSO).

Example 25

2-Fluoro-4-(4-pyridinyl)phenyl 2,3,4-tri-O-acetyl-5-thio-β-D-xylopyranoside By carrying out the operation analogously to example 3, starting from 4-bromo-2-fluorophenyl 2,3,4-tri-O-acetyl-5-thio-β-D-xylopyranoside, obtained according to preparation VI, and 4-pyridineboronic acid, the expected product is obtained in the form of a white solid with a yield of 51%.
M.p.=179° C.
$[\alpha]_D^{28}=14°$ (c=0.38; DMSO).

Example 26

2-Fluoro-4-(4-pyridinyl)phenyl 5-thio-β-D-xylopyranoside

By carrying out the operation analogously to example 4, starting with the product obtained according to example 25, 2-fluoro-4-(4-pyridinyl)phenyl 5-thio-β-D-xylo-pyranoside is obtained in the form of a white solid with a yield of 73%.
M.p.=215° C.
$[\alpha]_D^{28}=-24°$ (c=0.39; DMSO).

Example 27

5-Fluoro-2-(4-pyridinyl)phenyl 2,3,4-tri-O-acetyl-5-thio-β-D-xylopyranoside By carrying out the operation analogously to example 3, starting from 2-bromo-5-fluoro-phenyl 2,3,4-tri-O-acetyl-5-thio-β-D-xylopyranoside, obtained according to preparation V, and 4-pyridineboronic acid, the expected product is obtained in the form of a white solid with a yield of 79%.
M.p.=187° C.
$[\alpha]_D^{33}=-72°$ (c=0.24; DMSO).

Example 28

5-Fluoro-2-(4-pyridinyl)phenyl 5-thio-β-D-xylopyranoside

By carrying out the operation analogously to example 4, starting from the product obtained according to example 27, 5-fluoro-2-(4-pyridinyl)phenyl 5-thio-β-D-xylo-pyranoside is obtained in the form of a white solid with a yield of 33%.
M.p.=209° C.
$[\alpha]_D^{31}-80°$ (c=0.29; DMSO).

Example 29

3-(6-Methyl-3-pyridinyl)phenyl 5-thio-β-D-xylopyranoside 500 mg (1.12 mmol) of 3-bromophenyl 2,3,4-tri-O-acetyl-5-thio-β-D-xylopyranoside, obtained according to preparation VII, and 260 mg (1.68 mmol) of 6-methyl-3-pyridineboronic acid are placed in a suitable microwave reactor and then 500 mg of PS triphenylphosphine palladium resin (Argonaut) and 730 mg (2.24 mmol) of cesium carbonate are added. A mixture of 7 ml of dimethoxyethane and 3 ml of methanol is added and the reaction mixture is brought to 120° C. for 1 hour. After cooling, the reaction mixture is filtered and the filtrate is rinsed with methanol and concentrated under reduced pressure. The residue is purified by chromatography on a silica column, elution being carried out using a dichloromethane/methanol mixture (90/10; v/v), and then recrystallized from water. 3-(6-Methyl-3-pyridinyl)phenyl 5-thio-β-D-xylopyranoside is obtained in the form of a white solid with a yield of 65%.
M.p.=177° C.
$[\alpha]_D^{29}=-89°$ (c=0.13; DMSO).

Example 30

3-(6-Fluoro-3-pyridinyl)phenyl 2,3,4-tri-O-acetyl-5-thio-β-D-xylopyranoside By carrying out the operation analogously to example 3, starting from 3-iodophenyl 2,3,4-tri-O-acetyl-5-thio-β-D-xylopyranoside, obtained according to preparation I, and 6-fluoro-3-pyridineboronic acid, the expected product is obtained in the form of a white powder with a yield of 55%.
M.p.=115° C.
$[\alpha]_D^{29}=-15°$ (c=0.13; DMSO).

Example 31

3-(6-Fluoro-3-pyridinyl)phenyl 5-thio-β-D-xylopyranoside

By carrying out the operation analogously to example 4, starting from the product obtained according to example 30, 3-(6-fluoro-3-pyridinyl)phenyl 5-thio-β-D-xylo-pyranoside is obtained in the form of a white solid with a yield of 73%.
M.p.=170° C.
$[\alpha]_D^{29}=-70°$ (c=0.13; DMSO).

Example 32

3-(2-Methoxy-3-pyridinyl)phenyl 2,3,4-tri-O-acetyl-5-thio-β-D-xylopyranoside By carrying out the operation analogously to example 3, starting from 3-iodophenyl 2,3,4-tri-O-acetyl-5-thio-β-D-xylopyranoside, obtained according to preparation I, and 2-methoxy-3-pyridineboronic acid, the expected product is obtained in the form of a white powder with a yield of 66%.
M.p.=179° C.
$[\alpha]_D^{29}=-26°$ (c=0.40; DMSO).

Example 33

3-(2-Methoxy-3-pyridinyl)phenyl 5-thio-β-D-xylopyranoside

By carrying out the operation analogously to example 14, starting from the product obtained according to example 32, 3-(2-methoxy-3-pyridinyl)phenyl 5-thio-β-D-xylopyranoside is obtained in the form of a white solid with a yield of 64%.
M.p.=194° C.
$[\alpha]_D^{30}$=−62° (c=0.22; DMSO).

Example 34

3-(6-Cyano-3-pyridinyl)phenyl 2,3,4-tri-O-acetyl-5-thio-β-D-xylopyranoside

By carrying out the operation analogously to example 3, starting from 3-bromophenyl 2,3,4-tri-O-acetyl-5-thio-β-D-xylopyranoside, obtained according to preparation VII, and 6-cyano-3-pyridineboronic acid, the expected product is obtained in the form of a white solid with a yield of 45%.
M.p.=130° C.
$[\alpha]_D^{29}$=−6° (c=0.28; DMSO).

Example 35

3-(6-Cyano-3-pyridinyl)phenyl 5-thio-β-D-xylopyranoside

By carrying out the operation analogously to example 4, starting from the product obtained according to example 34, 3-(6-cyano-3-pyridinyl)phenyl 5-thio-β-D-xylo-pyranoside is obtained in the form of a white powder with a yield of 42%.
M.p.=179° C.
$[\alpha]_D^{30}$=−65° (c=0.21; DMSO).

Example 36

3-(4-Methyl-3-pyridinyl)phenyl 2,3,4-tri-O-acetyl-5-thio-β-D-xylopyranoside

A mixture composed of 1 g (5.81 mmol) of 3-bromo-4-methylpyridine, 8 ml of DME, 0.142 g (0.17 mmol) of the [1,1'-bis(diphenylphosphino)ferrocene]dichloropalladium-(II) complex with dichloromethane, 2.21 g (8.72 mmol) of bis(pinacolato)diboron and 1.7 g (17.4 mmol) of potassium acetate is heated at 120° C. for 60 minutes under an inert atmosphere using microwave radiation. After cooling, the reaction medium is filtered and 1.73 g (3.86 mmol) of 3-bromophenyl 2,3,4-tri-O-acetyl-5-thio-β-D-xylopyranoside, obtained according to preparation VII, 0.32 g (0.39 mmol) of the [1,1'-bis(diphenylphosphino)ferrocene]dichloropalladium(II) complex with dichloromethane and 5.8 ml of a 1M aqueous sodium carbonate solution are added to the filtrate. The mixture is again heated at 120° C. for 30 minutes using microwave radiation. The medium is cooled, diluted with water and extracted with ethyl acetate. The organic phase is washed with an aqueous sodium bicarbonate solution and then with water, dried over magnesium sulfate and concentrated under reduced pressure. The evaporation residue is purified by chromatography on a silica column, elution being carried out using a toluene/acetone mixture (80/20; v/v). The desired product is obtained in the form of an off-white solid with a yield of 21%.
M.p.=170° C.
$[\alpha]_D^{29}$=−14° (c=0.40; DMSO).

Example 37

3-(4-Methyl-3-pyridinyl)phenyl 5-thio-β-D-xylopyranoside

By carrying out the operation analogously to example 4, starting from the product obtained according to example 36, the expected compound is obtained in the form of an ecru-white powder with a yield of 55%.
M.p.=143° C.
$[\alpha]_D^{30}$=−52° (c=0.34; DMSO).

Example 38

3-(5-Methoxy-3-pyridinyl)phenyl 2,3,4-tri-O-acetyl-5-thio-β-D-xylopyranoside

By carrying out the operation analogously to example 36, starting from 3-bromo-5-methoxypyridine, the expected compound is obtained in the form of a white solid with a yield of 58%.
M.p.=167° C.
$[\alpha]_D^{29}$=−17° (c=0.39; DMSO).

Example 39

3-(5-Methoxy-3-pyridinyl)phenyl 5-thio-β-D-xylopyranoside

By carrying out the operation analogously to example 4, starting from the product obtained according to example 38, the expected compound is obtained in the form of a white solid with a yield of 82%.
M.p.=194° C.
$[\alpha]_D^{29}$=−69° (c=0.31; DMSO).

Example 40

3-(2-Methyl-3-pyridinyl)phenyl 2,3,4-tri-O-acetyl-5-thio-β-D-xylopyranoside

By carrying out the operation analogously to example 36, starting from 2-methyl-3-pyridinyl trifluoromethanesulfonate, the expected compound is obtained in the form of a beige solid with a yield of 38%.
M.p.=153° C.
$[\alpha]_D^{29}$=−19° (c=0.32; DMSO).

Example 41

3-(2-Methyl-3-pyridinyl)phenyl 5-thio-β-D-xylopyranoside

By carrying out the operation analogously to example 14, starting from the product obtained according to example 40, the expected compound is obtained in the form of an ecru-white solid with a yield of 58%.
M.p.=162-164° C.
$[\alpha]_D^{25}$=−78° (c=0.40; DMSO).

Example 42

3-(5-Methyl-3-pyridinyl)phenyl 2,3,4-tri-O-acetyl-5-thio-β-D-xylopyranoside

By carrying out the operation analogously to example 36, starting from 3-bromo-5-methylpyridine, the expected compound is obtained in the form of a beige solid with a yield of 31%.
M.p.=156° C.
$[\alpha]_D^{27}=-17°$ (c=0.20; DMSO).

Example 43

3-(5-Methyl-3-pyridinyl)phenyl 5-thio-β-D-xylopyranoside

By carrying out the operation analogously to example 14, starting from the product obtained according to example 42, the expected compound is obtained in the form of a white solid with a yield of 55%.
M.p.=239-240° C.
$[\alpha]_D^{29}=-76°$ (c=0.19; DMSO).

Example 44

3-(3-Fluoro-2-pyridinyl)phenyl 2,3,4-tri-O-acetyl-5-thio-β-D-xylopyranoside

By carrying out the operation analogously to example 36, starting from 2-chloro-3-fluoropyridine, the expected compound is obtained in the form of a fine white solid with a yield of 7%.
M.p.=51° C.
$[\alpha]_D^{29}=-32°$ (c=0.08; DMSO).

Example 45

3-(3-Fluoro-2-pyridinyl)phenyl 5-thio-β-D-xylopyranoside

By carrying out the operation analogously to example 4, starting from the product obtained according to example 44, the expected compound is obtained in the form of a white powder with a yield of 42%.
M.p.=150° C.
$[\alpha]_D^{29}=-87°$ (c=0.09; DMSO).

Example 46

3-(6-Methoxy-2-pyridinyl)phenyl 2,3,4-tri-O-acetyl-5-thio-β-D-xylopyranoside

By carrying out the operation analogously to example 36, starting from 2-bromo-6-methoxypyridine, the expected compound is obtained in the form of a beige powder with a yield of 50%.
M.p.=195° C. (crystallized from 2-propanol).
$[\alpha]_D^{27}=-21°$ (c=0.40; DMSO).

Example 47

3-(6-Methoxy-2-pyridinyl)phenyl 5-thio-β-D-xylopyranoside

By carrying out the operation analogously to example 4, starting from the product obtained according to example 46, the expected compound is obtained in the form of white needles with a yield of 63%.

M.p.=206° C. (crystallized from an ethanol/water mixture).
$[\alpha]_D^{27}=-86°$ (c=0.23; DMSO).

Example 48

3-(2,4-Dimethyl-5-thiazolyl)phenyl 2,3,4-tri-O-acetyl-5-thio-β-D-xylopyranoside a) 3-(4,4,5,5-tetramethyl-1,3,2-dioxaborolan-2-yl)phenyl 2,3,4-tri-O-acetyl-5-thio-β-D-xylopyranoside A mixture composed of 8 g (17.9 mmol) of 3-bromophenyl 2,3,4-tri-O-acetyl-5-thio-β-D-xylopyranoside, obtained according to preparation VII, 30 ml of DME, 0.438 g (0.537 mmol) of the [1,1'-bis(diphenylphosphino)ferrocene]dichloropalladium(II) complex with dichloromethane, 6.8 g (26.8 mmol) of bis(pinacolato)diboron and 5.2 g (53.7 mmol) of potassium acetate is heated at 150° C. for 35 minutes under an inert atmosphere using microwave radiation. The reaction mixture is subsequently concentrated under reduced pressure and the residual product is purified by chromatography on a silica column, elution being carried out using a toluene/isopropyl ether mixture (6/4; v/v). The desired product is obtained in the form of white crystals with a yield of 69%.
M.p.=198-200° C.
$[\alpha]_D^{27}=-16°$ (c=0.59; DMSO).

b) 3-(2,4-dimethyl-5-thiazolyl)phenyl 2,3,4-tri-O-acetyl-5-thio-β-D-xylopyranoside 0.9 g (1.82 mmol) of the compound obtained in stage a), 0.437 g (0.18 mmol) of 5-bromo-2,4-dimethylthiazole, 0.15 g (0.18 mmol) of the [1,1'-bis(diphenylphosphino)-ferrocene]dichloropalladium(II) complex with dichloromethane and 1.36 ml of a 2M aqueous potassium carbonate solution are mixed under an inert atmosphere. The mixture is heated at 120° C. for 30 minutes using microwave radiation. The medium is cooled, diluted with water and extracted with ethyl acetate. The organic phase is washed with an aqueous ammonium chloride solution and then with water, dried over magnesium sulfate and concentrated under reduced pressure. The evaporation residue is purified by chromatography on a silica column, elution being carried out using a dichloromethane/ethyl acetate mixture (gradient from 9/1 to 7/3; v/v). The expected product is obtained in the form of a pale yellow solid with a yield of 70%.
M.p.=114-120° C.
$[\alpha]_D^{23}=-23°$ (c=0.20; DMSO).

Example 49

3-(2,4-Dimethyl-5-thiazolyl)phenyl 5-thio-β-D-xylopyranoside

By carrying out the operation analogously to example 14, starting from the product obtained according to example 48, the expected compound is obtained in the form of off-white crystals with a yield of 78%.
M.p.=158-164° C.
$[\alpha]_D^{23}=-74°$ (c=0.63; DMSO).

Example 50

3-(4-Chloro-2-pyridinyl)phenyl 2,3,4-tri-O-acetyl-5-thio-β-D-xylopyranoside

By carrying out the operation analogously to example 48, starting from 2-bromo-4-chloropyridine, the expected compound is obtained in the form of white crystals with a yield of 35%.
M.p.=152° C. (crystallized from ethyl ether).
$[\alpha]_D^{26}=-19°$ (c=0.30; DMSO).

Example 51

3-(4-Chloro-2-pyridinyl)phenyl 5-thio-β-D-xylopyranoside

By carrying out the operation analogously to example 4, starting from the product obtained according to example 50, the expected compound is obtained in the form of an off-white solid with a yield of 94%.
M.p.=97-105° C.
$[\alpha]_D^{26}=-76°$ (c=0.18; DMSO).

Example 52

3-(5-Methyl-2-pyridinyl)phenyl 2,3,4-tri-O-acetyl-5-thio-β-D-xylopyranoside

By carrying out the operation analogously to example 48, starting from 2-bromo-5-methylpyridine, the expected compound is obtained in the form of white crystals with a yield of 28%.
M.p.=140° C. (crystallized from ethyl ether).
$[\alpha]_D^{26}=-11°$ (c=0.17; DMSO).

Example 53

3-(5-Methyl-2-pyridinyl)phenyl 5-thio-β-D-xylopyranoside

By carrying out the operation analogously to example 14, starting from the product obtained according to example 52, the expected compound is obtained in the form of a white solid with a yield of 76%.
M.p.=185-189° C.
$[\alpha]_D^{26}=-76°$ (c=0.15; DMSO).

Example 54

3-(6-Chloro-2-pyridinyl)phenyl 2,3,4-tri-O-acetyl-5-thio-β-D-xylopyranoside

By carrying out the operation analogously to example 48, starting from 2-bromo-6-chloropyridine, the expected compound is obtained in the form of white crystals with a yield of 71%.
M.p.=186-189° C. (crystallized from ethyl ether).
$[\alpha]_D^{27}=-19°$ (c=0.36; DMSO).

Example 55

3-(6-Chloro-2-pyridinyl)phenyl 5-thio-β-D-xylopyranoside

By carrying out the operation analogously to example 4, starting from the product obtained according to example 54, the expected compound is obtained in the form of white crystals with a yield of 44%.
M.p.=180-222° C.
$[\alpha]_D^{27}=-50°$ (c=0.36; DMSO).

Example 56

3-(Pyrazinyl)phenyl 2,3,4-tri-O-acetyl-5-thio-β-D-xylopyranoside

By carrying out the operation analogously to example 48, starting from iodopyrazine, the expected compound is obtained in the form of an off-white solid with a yield of 18%.
M.p.=92° C.
$[\alpha]_D^{30}=-13°$ (c=0.19; DMSO).

Example 57

3-(Pyrazinyl)phenyl 5-thio-β-D-xylopyranoside

By carrying out the operation analogously to example 14, starting from the product obtained according to example 56, the expected compound is obtained in the form of white crystals with a yield of 86%.
M.p.=206-209° C. (crystallized from methanol).
$[\alpha]_D^{30}=-80°$ (c=0.22; DMSO).

Example 58

3-(6-Hydroxy-3-pyridinyl)phenyl 2,3,4-tri-O-acetyl-5-thio-β-D-xylopyranoside

By carrying out the operation analogously to example 48, starting from the compound obtained according to preparation XII, and without isolating the 3-(4,4,5,5-tetramethyl-1,3,2-dioxaborolan-2-yl)phenyl 2,3,4-tri-O-acetyl-5-thio-β-D-xylopyranoside (the solution resulting from the preparation of this compound according to example 48a is used directly, after a simple filtration), the expected compound is obtained in the form of a white solid with a yield of 29%.
M.p.=131° C.
$[\alpha]_D^{30}=-15°$ (c=0.14; DMSO).

Example 59

3-(6-Hydroxy-3-pyridinyl)phenyl 5-thio-β-D-xylopyranoside

By carrying out the operation analogously to example 14, starting from the product obtained according to example 58, the expected compound is obtained in the form of a white solid with a yield of 44%.
M.p.=200° C.
$[\alpha]_D^{30}=-60°$ (c=0.10; DMSO).

Example 60

3-[1-Methyl-3-(trifluoromethyl)-1H-pyrazol-4-yl]phenyl 2,3,4-tri-O-acetyl-5-thio-β-D-xylopyranoside By carrying out the operation analogously to example 58, starting from 4-bromo-1-methyl-3-(trifluoromethyl)-1H-pyrazole, the expected compound is obtained in the form of a beige solid with a yield of 24%.
M.p.=131-133° C.
$[\alpha]_D^{29}=-25°$ (c=0.25; DMSO).

Example 61

3-[1-Methyl-3-(trifluoromethyl)1H-pyrazol-4-yl] phenyl 5-thio-β-D-xylopyranoside By carrying out the operation analogously to example 14, starting from the product obtained according to example 60, the expected compound is obtained in the form of a beige solid with a yield of 61%.
M.p.=182-185° C.
$[\alpha]_D^{29}$=−63° (c=0.22; DMSO).

Example 62

3-[5-Methyl-3-(trifluoromethyl)-1H-pyrazol-4-yl] phenyl 2,3,4-tri-O-acetyl-5-thio-β-D-xylopyranoside By carrying out the operation analogously to example 58, starting from 4-bromo-5-methyl-3-(trifluoromethyl)-1H-pyrazole, the expected compound is obtained in the form of a beige solid with a yield of 20%.
M.p.=194° C.
$[\alpha]_D^{30}$=−14° (c=0.19; DMSO).

Example 63

3-[5-Methyl-3-(trifluoromethyl)-1H-pyrazol-4-yl] phenyl 5-thio-β-D-xylopyranoside By carrying out the operation analogously to example 14, starting from the product obtained according to example 62, the expected compound is obtained in the form of a white solid with a yield of 60%.
M.p.=104-109° C.
$[\alpha]_D^{30}$=−53° (c=0.21; DMSO).

Example 64

3-(2-Thiazolyl)phenyl 2,3,4-tri-O-acetyl-5-thio-β-D-xylopyranoside

By carrying out the operation analogously to example 58, starting from 2-bromothiazole, the expected compound is obtained in the form of a beige solid with a yield of 7%.
M.p.=65° C.
$[\alpha]_D^{30}$=−17° (c=0.21; DMSO).

Example 65

3-(2-Thiazolyl)phenyl 5-thio-β-D-xylopyranoside

By carrying out the operation analogously to example 14, starting from the product obtained according to example 64, the expected compound is obtained in the form of white flakes with a yield of 76%.
M.p.=209-223° C.
$[\alpha]_D^{30}$=−90° (c=0.27; DMSO).

Example 66

3-(5-Fluoro-2-pyridinyl)phenyl 2,3,4-tri-O-acetyl-5-thio-β-D-xylopyranoside

By carrying out the operation analogously to example 58, starting from 2-bromo-5-fluoropyridine, the expected compound is obtained in the form of white crystals with a yield of 22%.
M.p.=113° C. (crystallized from ethyl ether).
$[\alpha]_D^{24}$=−20° (c=0.24; DMSO).

Example 67

3-(5-Fluoro-2-pyridinyl)phenyl 5-thio-β-D-xylopyranoside

By carrying out the operation analogously to example 14, starting from the product obtained according to example 66, the expected compound is obtained in the form of white flakes with a yield of 40%.
M.p.=168-201° C.
$[\alpha]_D^{30}$=−93° (c=0.30; DMSO).

Example 68

3-(3-Chloro-2-pyridinyl)phenyl 2,3,4-tri-O-acetyl-5-thio-β-D-xylopyranoside

By carrying out the operation analogously to example 58, starting from 2,3-dichloropyridine, the expected compound is obtained in the form of a white solid with a yield of 58%.
M.p.=148° C. (crystallized from ethyl ether).
$[\alpha]_D^{29}$=−32° (c=0.11; DMSO).

Example 69

3-(3-Chloro-2-pyridinyl)phenyl 5-thio-β-D-xylopyranoside

By carrying out the operation analogously to example 4, starting from the product obtained according to example 68, the expected compound is obtained in the form of brown needles with a yield of 83%.
M.p.=217° C. (crystallized from an ethanol/water mixture).
$[\alpha]_D^{29}$=−68° (c=0.41; DMSO).

Example 70

3-(5-Methyl-4-isoxazolyl)phenyl 2,3,4-tri-O-acetyl-5-thio-β-D-xylopyranoside By carrying out the operation analogously to example 58, starting from 5-methyl-4-iodoisoxazole, the expected compound is obtained in the form of a white solid with a yield of 69%.
M.p.=60° C.
$[\alpha]_D^{29}$=−43° (c=0.19; DMSO).

Example 71

3-(5-Methyl-4-isoxazolyl)phenyl 5-thio-β-D-xylopyranoside

By carrying out the operation analogously to example 4, starting from the product obtained according to example 70, the expected compound is obtained in the form of a white solid with a yield of 47%.
M.p.=180° C.
$[\alpha]_D^{28}$=−90° (c=0.23; DMSO).

Example 72

3-(4-Methyl-2-pyridinyl)phenyl 2,3,4-tri-O-acetyl-5-thio-β-D-xylopyranoside

By carrying out the operation analogously to example 58, starting from 2-bromo-4-methylpyridine, the expected compound is obtained in the form of a white solid with a yield of 20%.
M.p.=116° C.
$[\alpha]_D^{29}=-25°$ (c=0.26; DMSO).

Example 73

3-(4-Methyl-2-pyridinyl)phenyl 5-thio-β-D-xylopyranoside

By carrying out the operation analogously to example 4, starting from the product obtained according to example 72, the expected compound is obtained in the form of a beige powder with a yield of 23%.
M.p.=194° C.
$[\alpha]_D^{29}=-112°$ (c=0.25; DMSO).

Example 74

3-[6-(Dimethylamino)-3-pyridinyl]phenyl 2,3,4-tri-O-acetyl-5-thio-β-D-xylopyranoside By carrying out the operation analogously to example 58, starting from 5-bromo-2-(dimethylamino)pyridine, the expected compound is obtained in the form of a crude product used without further purification in the deacetylation stage.

Example 75

3-[6-(Dimethylamino)-3-pyridinyl]phenyl 5-thio-β-D-xylopyranoside

By carrying out the operation analogously to example 4, starting from the product obtained according to example 74, the expected compound is obtained in the form of a white solid with a yield of 20%.
M.p.=186° C.
$[\alpha]_D^{30}=-59°$ (c=0.17; DMSO).

Example 76

3-[6-(Dimethylamino)-3-pyridinyl]phenyl 5-thio-β-D-xylopyranoside (Hydrochloride)

A solution of 0.05 g (0.248 mmol) of the compound obtained according to example 75 in 3 ml of methanol is prepared and 0.2 ml (0.25 mmol) of a 1.25M solution of hydrochloric acid in methanol is added. The mixture is stirred at ambient temperature for 5 min and concentrated under reduced pressure. The evaporation residue is taken up in 5 ml of water and the solution obtained is lyophilized. The lyophilisate is crystallized from a methanol/ether mixture and then filtered off and dried. The expected compound is obtained in the form of a white solid with a yield of 91%.
M.p.=119° C.
$[\alpha]_D^{31}=-71°$ (c=0.18; DMSO).

Example 77

2-Chloro-5-(3,5-dimethyl-4-isoxazolyl)phenyl 2,3,4-tri-O-acetyl-5-thio-β-D-xylopyranoside By carrying out the operation analogously to example 58, starting from 5-bromo-2-chlorophenyl 2,3,4-tri-O-acetyl-5-thio-β-D-xylopyranoside, obtained according to preparation X, and 3,5-dimethyl-4-iodoisoxazole, the expected compound is obtained in the form of a crude product used without further purification in the deacetylation stage.

Example 78

2-Chloro-5-(3,5-dimethyl-4-isoxazolyl)phenyl 5-thio-β-D-xylopyranoside

By carrying out the operation analogously to example 4, starting from the product obtained according to example 77, the expected compound is obtained in the form of a white solid with a yield of 26%.
M.p.=194° C.
$[\alpha]_D^{31}=-64°$ (c=0.12; DMSO).

Example 79

2-Chloro-5-(5-methyl-4-isoxazolyl)phenyl 2,3,4-tri-O-acetyl-5-thio-β-D-xylopyranoside By carrying out the operation analogously to example 77, starting from 5-methyl-4-iodoisoxazole, the expected compound is obtained in the form of a crude product used without further purification in the deacetylation stage.

Example 80

2-Chloro-5-(5-methyl-4-isoxazolyl)phenyl 5-thio-β-D-xylopyranoside

By carrying out the operation analogously to example 4, starting from the product obtained according to example 79, the expected compound is obtained in the form of a white solid with a yield of 15%.
M.p.=183° C.
$[\alpha]_D^{31}=-28°$ (c=0.10; DMSO).

Example 81

2-Chloro-5-(2-pyridinyl)phenyl 2,3,4-tri-O-acetyl-5-thio-β-D-xylopyranoside

By carrying out the operation analogously to example 77, starting from 2-chloropyridine, the expected compound is obtained in the form of a crude product used without further purification in the deacetylation stage.

Example 82

2-Chloro-5-(2-pyridinyl)phenyl 5-thio-β-D-xylopyranoside

By carrying out the operation analogously to example 4, starting from the product obtained according to example 81, the expected compound is obtained in the form of a white solid with a yield of 18%.
M.p.=108° C.
$[\alpha]_{31}=-45°$ (c=0.10; DMSO).

Example 83

2,3-Difluoro-5-(2-pyridinyl)phenyl 2,3,4-tri-O-acetyl-5-thio-β-D-xylopyranoside

By carrying out the operation analogously to example 58, starting from 5-bromo-2,3-difluorophenyl 2,3,4-tri-O-acetyl-5-thio-β-D-xylopyranoside, obtained according to preparation VIII, and 2-chloropyridine, the expected compound is obtained in the form of a crude product used without further purification in the deacetylation stage.

Example 84

2,3-Difluoro-5-(2-pyridinyl)phenyl 5-thio-β-D-xylopyranoside

By carrying out the operation analogously to example 4, starting from the product obtained according to example 83, the expected compound is obtained in the form of a white solid with a yield of 39%.
M.p.=162° C.
$[\alpha]_D^{26}=-55°$ (c=0.20; DMSO).

Example 85

3-(6-Methyl-2-pyridinyl)phenyl 2,3,4-tri-O-acetyl-5-thio-β-D-xylopyranoside

By carrying out the operation analogously to example 58, starting from 2-chloro-6-methylpyridine, the expected compound is obtained in the form of a crude product used without further purification in the deacetylation stage.

Example 86

3-(6-Methyl-2-pyridinyl)phenyl 5-thio-β-D-xylopyranoside

By carrying out the operation analogously to example 4, starting from the product obtained according to example 85, the expected compound is obtained in the form of a yellow solid with a yield of 16%.
M.p.=143° C.
$[\alpha]_D^{29}=-34°$ (c=0.15; DMSO).

Example 87

3-(1,3,5-Trimethyl-1H-pyrazol-4-yl)phenyl 2,3,4-tri-O-acetyl-5-thio-β-D-xylopyranoside By carrying out the operation analogously to example 3, starting from 3-bromophenyl 2,3,4-tri-O-acetyl-5-thio-β-D-xylopyranoside, obtained according to preparation VII, and 4-(4,4,5,5-tetramethyl-1,3,2-dioxaborolan-2-yl)-1,3,5-trimethyl-1H-pyrazole, the expected product is obtained in the form of a white solid with a yield of 46%.
M.p.=164° C.
$[\alpha]_D^{29}=-32°$ (c=0.24; DMSO).

Example 88

3-(1,3,5-Trimethyl-1H-pyrazol-4-yl)phenyl 5-thio-β-D-xylopyranoside

By carrying out the operation analogously to example 4, starting from the product obtained according to example 87, the expected compound is obtained in the form of a white solid with a yield of 35%.
M.p.=95° C.
$[\alpha]_D^{32}=-77°$ (c=0.27; DMSO).

Example 89

3-(5-Chloro-3-pyridinyl)phenyl 2,3,4-tri-O-acetyl-5-thio-β-D-xylopyranoside

By carrying out the operation analogously to example 87, starting from 5-chloro-3-(4,4,5,5-tetramethyl-1,3,2-dioxaborolan-2-yl)pyridine, the expected product is obtained in the form of a white solid with a yield of 26%.
M.p.=139-141° C.
$[\alpha]_D^{29}=-23°$ (c=0.27; DMSO).

Example 90

3-(5-Chloro-3-pyridinyl)phenyl 5-thio-β-D-xylopyranoside

By carrying out the operation analogously to example 14, starting from the product obtained according to example 89, the expected compound is obtained in the form of a white solid with a yield of 89%.
M.p.=239-241° C.
$[\alpha]_D^{29}=-77°$ (c=0.19; DMSO).

Example 91

3-(5-Fluoro-3-pyridinyl)phenyl 2,3,4-tri-O-acetyl-5-thio-β-D-xylopyranoside

By carrying out the operation analogously to example 87, starting from 5-fluoro-3-(4,4,5,5-tetramethyl-1,3,2-dioxaborolan-2-yl)pyridine, the expected product is obtained in the form of a white solid with a yield of 44%.
M.p.=135° C.
$[\alpha]_D^{26}=-18°$ (c=0.31; DMSO).

Example 92

3-(5-Fluoro-3-pyridinyl)phenyl 5-thio-β-D-xylopyranoside

By carrying out the operation analogously to example 14, starting from the product obtained according to example 91, the expected compound is obtained in the form of a white solid with a yield of 90%.
M.p.=211-212° C.
$[\alpha]_D^{29}=-75°$ (c=0.41; DMSO).

Example 93

3-(1-Methyl-1H-pyrazol-4-yl)phenyl 2,3,4-tri-O-acetyl-5-thio-β-D-xylopyranoside

By carrying out the operation analogously to example 87, starting from 1-methyl-4-(4,4,5,5-tetramethyl-1,3,2-dioxaborolan-2-yl)pyrazole, the expected product is obtained in the form of a white solid with a yield of 50%.
M.p.=140° C.
$[\alpha]_D^{29}=-20°$ (c=0.18; DMSO).

Example 94

3-(1-Methyl-1H-pyrazol-4-yl)phenyl 5-thio-β-D-xylopyranoside

By carrying out the operation analogously to example 4, starting from the product obtained according to example 93, the expected compound is obtained in the form of a white solid with a yield of 39%.
M.p.=213° C.
$[\alpha]_D^{30} = 73°$ (c=0.25; DMSO).

Example 95

3-(3,5-Dimethyl-1H-pyrazol-4-yl)phenyl 2,3,4-tri-O-acetyl-5-thio-β-D-xylopyranoside By carrying out the operation analogously to example 87, starting from 3,5-dimethyl-4-(4,4,5,5-tetramethyl-1,3,2-dioxaborolan-2-yl)-1H-pyrazole, the expected product is obtained in the form of a white powder with a yield of 59%.
M.p.=195° C. (crystallized from ethyl ether).
$[\alpha]_D^{29} = -32°$ (c=0.21; DMSO).

Example 96

3-(3,5-Dimethyl-1H-pyrazol-4-yl)phenyl 5-thio-β-D-xylopyranoside

By carrying out the operation analogously to example 4, starting from the product obtained according to example 95, the expected compound is obtained in the form of a white powder with a yield of 55%.
M.p.=213° C. (crystallized from methanol).
$[\alpha]_D^{29} = -99°$ (c=0.28; DMSO).

Example 97

2-Chloro-5-(1-methyl-1H-pyrazol-4-yl)phenyl 2,3,4-tri-O-acetyl-5-thio-β-D-xylopyranoside By carrying out the operation analogously to example 87, starting from 1-methyl-4-(4,4,5,5-tetramethyl-1,3,2-dioxaborolan-2-yl)-1H-pyrazole and 5-bromo-2-chlorophenyl 2,3,4-tri-O-acetyl-5-thio-β-D-xylopyranoside obtained according to preparation X, the expected product is obtained and is reacted further without additional purification in order to obtain the nonacetylated xyloside.

Example 98

2-Chloro-5-(1-methyl-1H-pyrazol-4-yl)phenyl 5-thio-β-D-xylopyranoside

By carrying out the operation analogously to example 4, starting from the product obtained according to example 97, the expected compound is obtained in the form of a white solid with a yield of 54%.
M.p.=158° C.
$[\alpha]_D^{30} = -54°$ (c=0.24; DMSO).

Example 99

2,3-Difluoro-5-(1-methyl-1H-pyrazol-4-yl)phenyl 2,3,4-tri-O-acetyl-5-thio-β-D-xylopyranoside By carrying out the operation analogously to example 97, starting from 5-bromo-2,3-difluorophenyl 2,3,4-tri-O-acetyl-5-thio-β-D-xylopyranoside, obtained according to preparation VIII, the expected product is obtained and is reacted further without additional purification in order to obtain the nonacetylated xyloside.

Example 100

2,3-Difluoro-5-(1-methyl-1H-pyrazol-4-yl)phenyl 5-thio-β-D-xylopyranoside

By carrying out the operation analogously to example 4, starting from the product obtained according to example 99, the expected compound is obtained in the form of a white solid with a yield of 35%.
M.p.=184° C.
$[\alpha]_D^{27} = -44°$ (c=0.18; DMSO).

Example 101

2-Chloro-5-(3-pyridinyl)phenyl 2,3,4-tri-O-acetyl-5-thio-β-D-xylopyranoside

By carrying out the operation analogously to example 3, starting from 5-bromo-2-chlorophenyl 2,3,4-tri-O-acetyl-5-thio-β-D-xylopyranoside, obtained according to preparation X, the expected product is obtained in the form of a pink powder with a yield of 57%.
M.p.=155° C. (crystallized from ethyl ether).
$[\alpha]_D^{30} = -14°$ (c=0.30; DMSO).

Example 102

2-Chloro-5-(3-pyridinyl)phenyl 5-thio-β-D-xylopyranoside

By carrying out the operation analogously to example 4, starting from the product obtained according to example 101, the expected compound is obtained in the form of a white powder with a yield of 99%.
M.p.=172° C.
$[\alpha]_D^{30} = -43°$ (c=0.60; DMSO).

Example 103

4-Chloro-3-(3-pyridinyl)phenyl 2,3,4-tri-O-acetyl-5-thio-β-D-xylopyranoside

By carrying out the operation analogously to example 3, starting from 3-bromo-4-chlorophenyl 2,3,4-tri-O-acetyl-5-thio-β-D-xylopyranoside, obtained according to preparation IX, the expected product is obtained in the form of a white powder with a yield of 50%.
M.p.=133° C. (crystallized from isopropyl ether).
$[\alpha]_D^{27} = -8°$ (c=0.23; DMSO).

Example 104

4-Chloro-3-(3-pyridinyl)phenyl 5-thio-β-D-xylopyranoside

By carrying out the operation analogously to example 4, starting with a product obtained according to example 103, the expected compound is obtained in the form of a white powder with a yield of 27%.
M.p.=139° C.
$[\alpha]_D^{27} = -59°$ (c=0.21; DMSO).

Example 105

2,3-Difluoro-5-(3-pyridinyl)phenyl 2,3,4-tri-O-acetyl-5-thio-β-D-xylopyranoside

By carrying out the operation analogously to example 3, starting from 5-bromo-2,3-difluorophenyl 2,3,4-tri-O-acetyl-5-thio-β-D-xylopyranoside, obtained according to preparation VIII, the expected product is obtained in the form of a white powder with a yield of 87%.

M.p.=134° C.
$[\alpha]_D^{26}$=−23° (c=0.23; CHCl$_3$).

Example 106

2,3-Difluoro-5-(3-pyridinyl)phenyl 5-thio-β-D-xylopyranoside

By carrying out the operation analogously to example 14, starting from the product obtained according to example 105, the expected compound is obtained in the form of a white powder with a yield of 93%.

M.p.=177° C.
$[\alpha]_D^{26}$=−31° (c=0.32; DMSO).

Example 107

2-Fluoro-5-(3-pyridinyl)phenyl 2,3,4-tri-O-acetyl-5-thio-β-D-xylopyranoside

By carrying out the operation analogously to example 3, starting from 5-bromo-2-fluorophenyl 2,3,4-tri-O-acetyl-5-thio-β-D-xylopyranoside, obtained according to preparation XI, the expected product is obtained in the form of a white solid with a yield of 25%.

M.p.=152° C.
$[\alpha]_D^{33}$=14° (c=0.40; DMSO).

Example 108

2-Fluoro-5-(3-pyridinyl)phenyl 5-thio-β-D-xylopyranoside

By carrying out the operation analogously to example 4, starting from the product obtained according to example 107, the expected compound is obtained in the form of a fluffy white solid with a yield of 71%.

M.p.=100° C. (crystallized from water).
$[\alpha]_D^{35}$=−42° (c=0.50; DMSO).

Example 109

3-(2-Fluoro-4-pyridinyl)phenyl 2,3,4-tri-O-acetyl-5-thio-β-D-xylopyranoside

By carrying out the operation analogously to example 3, starting from 3-bromophenyl 2,3,4-tri-O-acetyl-5-thio-β-D-xylopyranoside, obtained according to preparation VII, and 2-fluoro-4-pyridineboronic acid, the expected product is obtained in the form of a white solid with a yield of 52%.

M.p.=117° C.
$[\alpha]_D^{29}$=−19° (c=0.19; DMSO).

Example 110

3-(2-Fluoro-4-pyridinyl)phenyl 5-thio-β-D-xylopyranoside

By carrying out the operation analogously to example 14, starting from the product obtained according to example 109, the expected compound is obtained in the form of a white solid with a yield of 74%.

M.p.=199° C.
$[\alpha]_D^{30}$=−82° (c=0.19; DMSO).

Example 111

3-(3-Chloro-4-pyridinyl)phenyl 2,3,4-tri-O-acetyl-5-thio-β-D-xylopyranoside

By carrying out the operation analogously to example 109, starting from 3-chloro-4-pyridineboronic acid, the expected product is obtained in the form of a white solid with a yield of 12%.

M.p.=169-171° C.
$[\alpha]_D^{25}$=−23° (c=0.24; DMSO).

Example 112

3-(3-Chloro-4-pyridinyl)phenyl 5-thio-β-D-xylopyranoside

By carrying out the operation analogously to example 29, starting from 3-chloro-4-pyridineboronic acid, the expected compound is obtained in the form of a white solid with a yield of 23%.

M.p.=158-161° C.
$[\alpha]_D^{25}$=−63° (c=0.37; DMSO).

Example 113

3-(2-Chloro-3-pyridinyl)phenyl 2,3,4-tri-O-acetyl-5-thio-β-D-xylopyranoside

By carrying out the operation analogously to example 109, starting from 2-chloro-3-pyridineboronic acid, the expected product is obtained in the form of a white solid with a yield of 48%.

M.p.=146-147° C.
$[\alpha]_D^{29}$=−20° (c=0.34; DMSO).

Example 114

3-(2-Chloro-3-pyridinyl)phenyl 5-thio-β-D-xylopyranoside

By carrying out the operation analogously to example 14, starting from the compound obtained according to example 113, the expected compound is obtained in the form of a white solid with a yield of 34%.

M.p.=130° C.
$[\alpha]_D^{29}$=−70° (c=0.27; DMSO).

Example 115

3-(2-Thienyl)phenyl 2,3,4-tri-O-acetyl-5-thio-β-D-xylopyranoside

By carrying out the operation analogously to example 109, starting from 2-thiopheneboronic acid, the expected product is obtained in the form of a white solid with a yield of 18%.

M.p.=122-123° C.
$[\alpha]_D^{28}$=−15° (c=0.21; DMSO).

Example 116

3-(2-Thienyl)phenyl 5-thio-β-D-xylopyranoside

By carrying out the operation analogously to example 14, starting from the compound obtained according to example 115, the expected compound is obtained in the form of a beige solid with a yield of 92%.
M.p.=165-166° C.
$[\alpha]_D^{28}=-65°$ (c=0.22; DMSO).

Example 117

3-(2-Fluoro-3-pyridinyl)phenyl 2,3,4-tri-O-acetyl-5-thio-β-D-xylopyranoside

By carrying out the operation analogously to example 109, starting from 2-fluoro-3-pyridineboronic acid, the expected product is obtained in the form of a white solid with a yield of 78%.
M.p.=116° C.
$[\alpha]_D^{27}=-28°$ (c=0.24; DMSO).

Example 118

3-(2-Fluoro-3-pyridinyl)phenyl 5-thio-β-D-xylopyranoside

By carrying out the operation analogously to example 4, starting from the compound obtained according to example 117, the expected compound is obtained in the form of a white solid with a yield of 25%.
M.p.=160° C.
$[\alpha]_D^{30}=-74°$ (c=0.31; DMSO).

Example 119

3-(3-Thienyl)phenyl 2,3,4-tri-O-acetyl-5-thio-β-D-xylopyranoside

By carrying out the operation analogously to example 13, starting from 3-bromophenyl 2,3,4-tri-O-acetyl-5-thio-β-D-xylopyranoside, obtained according to preparation VII, and 3-thiopheneboronic acid, the expected product is obtained in the form of white crystals with a yield of 26%.
M.p.=111° C. (crystallized from isopropyl ether).
$[\alpha]_D^{26}=-11°$ (c=0.27; DMSO).

Example 120

3-(3-Thienyl)phenyl 5-thio-β-D-xylopyranoside

By carrying out the operation analogously to example 14, starting from the compound obtained according to example 119, the expected compound is obtained in the form of white crystals with a yield of 38%.
M.p.=182° C.
$[\alpha]_D^{27}=-50°$ (c=0.31; DMSO).

Example 121

3-(5-Methyl-2-furyl)phenyl 2,3,4-tri-O-acetyl-5-thio-β-D-xylopyranoside

By carrying out the operation analogously to example 109, starting from 5-methyl-2-furanboronic acid, the expected product is obtained in the form of a white solid with a yield of 31%.
M.p.=132° C.
$[\alpha]_D^{28}=-10°$ (c=0.27; DMSO).

Example 122

3-(5-Methyl-2-furyl)phenyl 5-thio-β-D-xylopyranoside

By carrying out the operation analogously to example 4, starting from the compound obtained according to example 121, the expected compound is obtained in the form of a white solid with a yield of 46%.
M.p.=156° C.
$[\alpha]_D^{29}=-75°$ (c=0.22; DMSO).

Example 123

3-(6-Chloro-3-pyridinyl)phenyl 2,3,4-tri-O-acetyl-5-thio-β-D-xylopyranoside

By carrying out the operation analogously to example 109, starting from 6-chloro-3-pyridineboronic acid, the expected product is obtained in the form of a white foam with a yield of 24%.
M.p.=129° C.
$[\alpha]_D^{28}=-14°$ (c=0.29; DMSO).

Example 124

3-(6-Chloro-3-pyridinyl)phenyl 5-thio-β-D-xylopyranoside

By carrying out the operation analogously to example 4, starting from the compound obtained according to example 123, the expected compound is obtained in the form of a white solid with a yield of 83%.
M.p.=189° C.
$[\alpha]_D^{30}=-67°$ (c=0.44; DMSO).

Example 125

3-(6-Methoxy-3-pyridinyl)phenyl 2,3,4-tri-O-acetyl-5-thio-β-D-xylopyranoside

By carrying out the operation analogously to example 109, starting from 6-methoxy-3-pyridineboronic acid, the expected product is obtained in the form of a white solid with a yield of 47%.
M.p.=132° C.
$[\alpha]_D^{30}=-7°$ (c=0.26; DMSO).

Example 126

3-(6-Methoxy-3-pyridinyl)phenyl 5-thio-β-D-xylopyranoside

By carrying out the operation analogously to example 4, starting from the compound obtained according to example 125, the expected compound is obtained in the form of a white solid with a yield of 74%.
M.p.=174° C.
$[\alpha]_D^{29}=-80°$ (c=0.31; DMSO).

Example 127

3-(3,5-Dimethyl-4-isoxazolyl)phenyl 2,3,4-tri-O-acetyl-5-thio-β-D-xylopyranoside By carrying out the operation analogously to example 13, starting from 3-iodophenyl 2,3,4-tri-O-acetyl-5-thio-β-D- xylopyranoside, obtained according to preparation I, and 3,5-dimethyl-4-isoxazoleboronic acid, the expected product is obtained in the form of a pink powder with a yield of 53%.
M.p.=167-169° C.
$[\alpha]_D^{28}$=−31° (c=0.13; DMSO).

Example 128

3-(3,5-Dimethyl-4-isoxazolyl)phenyl 5-thio-β-D-xylopyranoside

By carrying out the operation analogously to example 14, starting from the compound obtained according to example 127, the expected compound is obtained in the form of a white solid with a yield of 66%.
M.p.=170° C.
$[\alpha]_D^{28}$=−86° (c=0.30; DMSO).

Example 129

2,3-Difluoro-5-(4-pyridinyl)phenyl 2,3,4-tri-O-acetyl-5-thio-β-D-xylopyranoside

By carrying out the operation analogously to example 3, starting from 5-bromo-2,3-difluorophenyl 2,3,4-tri-O-acetyl-5-thio-β-D-xylopyranoside, obtained according to preparation VIII, and 4-pyridineboronic acid, the expected product is obtained in the form of a white powder with a yield of 81%.
M.p.=139° C.
$[\alpha]_D^{28}$=−36° (c=0.33; CHCl$_3$).

Example 130

2,3-Difluoro-5-(4-pyridinyl)phenyl 5-thio-β-D-xylopyranoside

By carrying out the operation analogously to example 14, starting from the product obtained according to example 129, the expected compound is obtained in the form of a cream powder with a yield of 99%.
M.p.=151° C.
$[\alpha]_D^{29}$=−52° (c=0.35; MeOH).

Example 131

2,3-Difluoro-5-(3,5-dimethyl-4-isoxazolyl)phenyl 2,3,4-tri-O-acetyl-5-thio-β-D-xylopyranoside By carrying out the operation analogously to example 129, starting from 3,5-dimethyl-4-isoxazoleboronic acid, the expected product is obtained and is reacted further without additional purification in order to obtain the nonacetylated xyloside.

Example 132

2,3-Difluoro-5-(3,5-dimethyl-4-isoxazolyl)phenyl 5-thio-β-D-xylopyranoside

By carrying out the operation analogously to example 4, starting from the product obtained according to example 131, the expected compound is obtained in the form of a white solid with a yield of 30%.
M.p.=171° C.
$[\alpha]_D^{30}$=−82° (c=0.10; DMSO).

Example 133

2,3-Difluoro-5-(6-methyl-3-pyridinyl)phenyl 2,3,4-tri-O-acetyl-5-thio-β-D-xylopyranoside By carrying out the operation analogously to example 129, starting from 6-methyl-3-pyridineboronic acid, the expected product is obtained and is reacted further without additional purification in order to obtain the nonacetylated xyloside.

Example 134

2,3-Difluoro-5-(6-methyl-3-pyridinyl)phenyl 5-thio-β-D-xylopyranoside

By carrying out the operation analogously to example 4, starting from the product obtained according to example 133, the expected compound is obtained in the form of a white solid with a yield of 56%.
M.p.=186° C.
$[\alpha]_D^{33}$=−46° (c=0.15; DMSO).

Example 135

2,3-Difluoro-5-(2-methyl-4-pyridinyl)phenyl 2,3,4-tri-O-acetyl-5-thio-β-D-xylopyranoside By carrying out the operation analogously to example 129, starting from 2-methyl-4-pyridineboronic acid, the expected product is obtained and is reacted further without additional purification in order to obtain the nonacetylated xyloside.

Example 136

2,3-Difluoro-5-(2-methyl-4-pyridinyl)phenyl 5-thio-β-D-xylopyranoside

By carrying out the operation analogously to example 4, starting from the product obtained according to example 135, the expected compound is obtained in the form of a white solid with a yield of 25%.
M.p.=171° C.
$[\alpha]_D^{30}$=−45° (c=0.10; DMSO).

Example 137

2,3-Difluoro-5-(2-methoxy-3-pyridinyl)phenyl 2,3,4-tri-O-acetyl-5-thio-β-D-xylopyranoside By carrying out the operation analogously to example 129, starting from 2-methoxy-3-pyridineboronic acid, the expected product is obtained and is reacted further without additional purification in order to obtain the nonacetylated xyloside.

Example 138

2,3-Difluoro-5-(2-methoxy-3-pyridinyl)phenyl 5-thio-β-D-xylopyranoside

By carrying out the operation analogously to example 4, starting from the product obtained according to example 137, the expected compound is obtained in the form of a white solid with a yield of 75%.
M.p.=127° C.
$[\alpha]_D^{27}$=−45° (c=0.16; DMSO).

Example 139

2,3-Difluoro-5-(2-fluoro-3-pyridinyl)phenyl 2,3,4-tri-O-acetyl-5-thio-β-D-xylopyranoside By carrying out the operation analogously to example 129, starting from 2-fluoro-3-pyridineboronic acid, the expected product is obtained and is reacted further without additional purification in order to obtain the nonacetylated xyloside.

Example 140

2,3-Difluoro-5-(2-fluoro-3-pyridinyl)phenyl 5-thio-β-D-xylopyranoside

By carrying out the operation analogously to example 4, starting from the product obtained according to example 139, the expected compound is obtained in the form of a white solid with a yield of 21%.
M.p.=170° C.
$[\alpha]_D^{29}=-18°$ (c=0.12; DMSO).

Example 141

2,3-Difluoro-5-(5-pyrimidinyl)phenyl 2,3,4-tri-O-acetyl-5-thio-β-D-xylopyranoside By carrying out the operation analogously to example 129, starting from 5-pyrimidineboronic acid, the expected product is obtained and is reacted further without additional purification in order to obtain the nonacetylated xyloside.

Example 142

2,3-Difluoro-5-(5-pyrimidinyl)phenyl 5-thio-β-D-xylopyranoside

By carrying out the operation analogously to example 4, starting from the product obtained according to example 141, the expected compound is obtained in the form of a white solid with a yield of 20%.
M.p.=191° C.
$[\alpha]_D^{29}=-12°$ (c=0.10; DMSO).

Example 143

2,3-Difluoro-5-(2-fluoro-4-pyridinyl)phenyl 2,3,4-tri-O-acetyl-5-thio-β-D-xylopyranoside By carrying out the operation analogously to example 129, starting from 2-fluoro-4-pyridineboronic acid, the expected product is obtained and is reacted further without additional purification in order to obtain the nonacetylated xyloside.

Example 144

2,3-Difluoro-5-(2-fluoro-4-pyridinyl)phenyl 5-thio-β-D-xylopyranoside

By carrying out the operation analogously to example 4, starting from the product obtained according to example 143, the expected compound is obtained in the form of a white powder with a yield of 68%.
M.p.=184° C.
$[\alpha]_D^{30}=-37°$ (c=0.10; DMSO).

Example 145

2,3-Difluoro-5-(6-fluoro-3-pyridinyl)phenyl 2,3,4-tri-O-acetyl-5-thio-β-D-xylopyranoside By carrying out the operation analogously to example 129, starting from 6-fluoro-3-pyridineboronic acid, the expected product is obtained and is reacted further without additional purification in order to obtain the nonacetylated xyloside.

Example 146

2,3-Difluoro-5-(6-fluoro-3-pyridinyl)phenyl 5-thio-β-D-xylopyranoside

By carrying out the operation analogously to example 4, starting from the product obtained according to example 145, the expected compound is obtained in the form of an off-white solid with a yield of 53%.
M.p.=179° C.
$[\alpha]_D^{30}=-121°$ (c=0.10; DMSO).

Example 147

2-(3,5-Dimethyl-4-isoxazolyl)phenyl 2,3,4-tri-O-acetyl-5-thio-β-D-xylopyranoside By carrying out the operation analogously to example 3, starting from 2-bromophenyl 2,3,4-tri-O-acetyl-5-thio-β-D-xylopyranoside, obtained according to preparation IV, and 3,5-dimethyl-4-isoxazoleboronic acid, the expected compound is obtained in the form of a white solid with a yield of 76%.
M.p.=136-138° C.
$[\alpha]_D^{28}=-61°$ (c=0.13; DMSO).

Example 148

2-(3,5-Dimethyl-4-isoxazolyl)phenyl 5-thio-β-D-xylopyranoside

By carrying out the operation analogously to example 14, starting from the product obtained according to example 147, the expected compound is obtained in the form of a white powder with a yield of 99%.
M.p.=110-117° C.
$[\alpha]_D^{228}=-55°$ (c=0.24; DMSO).

Example 149

2-Fluoro-4-(3,5-dimethyl-4-isoxazolyl)phenyl 2,3,4-tri-O-acetyl-5-thio-β-D-xylopyranoside By carrying out the operation analogously to example 3, starting from 4-bromo-2-fluorophenyl 2,3,4-tri-O-acetyl-5-thio-β-D-xylopyranoside obtained according to preparation VI, and 3,5-dimethyl-4-isoxazoleboronic acid, the expected compound is obtained in the form of a white solid with a yield of 59%.
M.p.=177° C.
$[\alpha]_D^{26}=-1°$ (c=0.26; DMSO).

Example 150

2-Fluoro-4-(3,5-dimethyl-4-isoxazolyl)phenyl 5-thio-β-D-xylopyranoside

By carrying out the operation analogously to example 4, starting from the product obtained according to example 149, the expected compound is obtained in the form of a white solid with a yield of 74%.
M.p.=140° C.
$[\alpha]_D^{30}=-41°$ (c=0.37; DMSO).

Example 151

2-Fluoro-4-(3-furyl)phenyl 2,3,4-tri-O-acetyl-5-thio-β-D-xylopyranoside

By carrying out the operation analogously to example 149, starting from 3-furanboronic acid, the expected compound is obtained in the form of a white solid with a yield of 95%.
M.p.=137° C.
$[\alpha]_D^{28}=1°$ (c=0.37; DMSO).

Example 152

2-Fluoro-4-(3-furyl)phenyl 5-thio-β-D-xylopyranoside

By carrying out the operation analogously to example 4, starting from the product obtained according to example 151, the expected compound is obtained in the form of a white solid with a yield of 40%.
M.p.=155° C.
$[\alpha]_D^{28}=-26°$ (c=0.47; DMSO).

Example 153

5-Fluoro-2-(3-furyl)phenyl 2,3,4-tri-O-acetyl-5-thio-β-D-xylopyranoside

By carrying out the operation analogously to example 3, starting from 3-furanboronic acid, the expected compound is obtained in the form of a white solid with a yield of 61%.
$[\alpha]_D^{33}=-93°$ (c=0.27; DMSO).

Example 154

5-Fluoro-2-(3-furyl)phenyl 5-thio-β-D-xylopyranoside

By carrying out the operation analogously to example 4, starting from the product obtained according to example 153, the expected compound is obtained in the form of a white solid with a yield of 91%.
M.p.=139° C.
$[\alpha]_D^{31}=-105°$ (c=0.28; DMSO).

Example 155

5-Fluoro-2-(3,5-dimethyl-4-isoxazolyl)phenyl 2,3,4-tri-O-acetyl-5-thio-β-D-xylopyranoside By carrying out the operation analogously to example 3, starting from 3,5-dimethyl-4-isoxazoleboronic acid, the expected compound is obtained in the form of a beige solid with a yield of 53%.
$[\alpha]_D^{30}=-64°$ (c=0.24; DMSO).

Example 156

5-Fluoro-2-(3,5-dimethyl-4-isoxazolyl)phenyl 5-thio-β-D-xylopyranoside

By carrying out the operation analogously to example 4, starting from the product obtained according to example 155, the expected compound is obtained in the form of a white solid with a yield of 78%.
M.p.=192° C.
$[\alpha]_D^{31}=-50°$ (c=0.19; DMSO).

Example 157

2-Chloro-5-(2-methyl-4-pyridinyl)phenyl 2,3,4-tri-O-acetyl-5-thio-β-D-xylopyranoside By carrying out the operation analogously to example 3, starting from 5-bromo-2-chlorophenyl 2,3,4-tri-O-acetyl-5-thio-β-D-xylopyranoside, obtained according to preparation X, and 2-methyl-4-pyridineboronic acid, the expected product is obtained and is reacted further without additional purification in order to obtain the nonacetylated xyloside.

Example 158

2-Chloro-5-(2-methyl-4-pyridinyl)phenyl 5-thio-β-D-xylopyranoside

By carrying out the operation analogously to example 4, starting from the product obtained according to example 157, the expected compound is obtained in the form of a white solid with a yield of 31%.
M.p.=137° C.
$[\alpha]_D^{31}=-49°$ (c=0.11; DMSO).

Example 159

2-Chloro-5-(6-methyl-3-pyridinyl)phenyl 2,3,4-tri-O-acetyl-5-thio-β-D-xylopyranoside By carrying out the operation analogously to example 157, starting from 6-methyl-3-pyridineboronic acid, the expected product is obtained and is reacted further without additional purification in order to obtain the nonacetylated xyloside.

Example 160

2-Chloro-5-(6-methyl-3-pyridinyl)phenyl 5-thio-β-D-xylopyranoside

By carrying out the operation analogously to example 4, starting from the product obtained according to example 159, the expected compound is obtained in the form of a white solid with a yield of 48%.
M.p.=201° C.
$[\alpha]_{30}=-84°$ (c=0.25; DMSO).

Example 161

2-Chloro-5-(2-methoxy-3-pyridinyl)phenyl 2,3,4-tri-O-acetyl-5-thio-β-D-xylopyranoside By carrying out the operation analogously to example 157, starting from 2-methoxy-3-pyridineboronic acid, the expected product is obtained and is reacted further without additional purification in order to obtain the nonacetylated xyloside.

Example 162

2-Chloro-5-(2-methoxy-3-pyridinyl)phenyl 5-thio-β-D-xylopyranoside

By carrying out the operation analogously to example 4, starting from the product obtained according to example 161, the expected compound is obtained in the form of a white solid with a yield of 43%.
M.p.=119° C.
$[\alpha]_D^{30}=-55°$ (c=0.14; DMSO).

Example 163

2-Chloro-5-(2-fluoro-4-pyridinyl)phenyl 2,3,4-tri-O-acetyl-5-thio-β-D-xylopyranoside By carrying out the operation analogously to example 157, starting from 2-fluoro-4-pyridineboronic acid, the expected product is obtained and is reacted further without additional purification in order to obtain the nonacetylated xyloside.

Example 164

2-Chloro-5-(2-fluoro-4-pyridinyl)phenyl 5-thio-β-D-xylopyranoside

By carrying out the operation analogously to example 4, starting from the product obtained according to example 163, the expected compound is obtained in the form of a white solid with a yield of 40%.
M.p.=162° C.
$[\alpha]_D^{30}=-65°$ (c=0.16; DMSO).

Example 165

2-Chloro-5-(2-fluoro-3-pyridinyl)phenyl 2,3,4-tri-O-acetyl-5-thio-β-D-xylopyranoside By carrying out the operation analogously to example 157, starting from 2-fluoro-3-pyridineboronic acid, the expected product is obtained and is reacted further without additional purification in order to obtain the nonacetylated xyloside.

Example 166

2-Chloro-5-(2-fluoro-3-pyridinyl)phenyl 5-thio-β-D-xylopyranoside

By carrying out the operation analogously to example 4, starting from the product obtained according to example 165, the expected compound is obtained in the form of a white solid with a yield of 15%.
M.p.=165° C.
$[\alpha]_D^{30}=-49°$ (c=0.10; DMSO).

Example 167

2-Chloro-5-(4-pyridinyl)phenyl 2,3,4-tri-O-acetyl-5-thio-β-D-xylopyranoside

By carrying out the operation analogously to example 157, starting from 4-pyridineboronic acid, the expected product is obtained and is reacted further without additional purification in order to obtain the nonacetylated xyloside.

Example 168

2-Chloro-5-(4-pyridinyl)phenyl 5-thio-β-D-xylopyranoside

By carrying out the operation analogously to example 4, starting from the product obtained according to example 167, the expected compound is obtained in the form of a white solid with a yield of 29%.
M.p.=189° C.
$[\alpha]_D^{30}=-68°$ (c=0.16; DMSO).

Example 169

2-Chloro-5-(5-pyrimidinyl)phenyl 2,3,4-tri-O-acetyl-5-thio-β-D-xylopyranoside

By carrying out the operation analogously to example 157, starting from 5-pyrimidineboronic acid, the expected product is obtained and is reacted further without additional purification in order to obtain the nonacetylated xyloside.

Example 170

2-Chloro-5-(5-pyrimidinyl)phenyl 5-thio-β-D-xylopyranoside

By carrying out the operation analogously to example 4, starting from the product obtained according to example 169, the expected compound is obtained in the form of a white solid with a yield of 31%.
M.p.=186° C.
$[\alpha]_D^{27}=-58°$ (c=0.24; DMSO).

Example 171

2-Chloro-5-(6-fluoro-3-pyridinyl)phenyl 2,3,4-tri-O-acetyl-5-thio-β-D-xylopyranoside By carrying out the operation analogously to example 157, starting from 6-fluoro-3-pyridineboronic acid, the expected product is obtained and is reacted further without additional purification in order to obtain the nonacetylated xyloside.

Example 172

2-Chloro-5-(6-fluoro-3-pyridinyl)phenyl 5-thio-β-D-xylopyranoside

By carrying out the operation analogously to example 4, starting from the product obtained according to example 171, the expected compound is obtained in the form of a white solid with a yield of 38%.
M.p.=185° C.
$[\alpha]_D^{26}=-59°$ (c=0.12; DMSO).

Example 173

4-(2-Furyl)phenyl 2,3,4-tri-O-acetyl-5-thio-β-D-xylopyranoside

By carrying out the operation analogously to example 3, starting from 4-iodophenyl 2,3,4-tri-O-acetyl-5-thio-β-D-xylopyranoside, obtained according to preparation II, and 2-furanboronic acid, the expected product is obtained and is reacted further without additional purification in order to obtain the nonacetylated xyloside.

Example 174

4-(2-Furyl)phenyl 5-thio-β-D-xylopyranoside

By carrying out the operation analogously to example 14, starting from the product obtained according to example 173, the expected compound is obtained in the form of a yellow powder with a yield of 30%.
M.p.=200° C.
$[\alpha]_D^{31}=-49°$ (c=0.20; CH$_3$OH).

Example 175

3-(2-Furyl)phenyl 2,3,4-tri-O-acetyl-5-thio-β-D-xylopyranoside

By carrying out the operation analogously to example 3, starting from 3-iodophenyl 2,3,4-tri-O-acetyl-5-thio-β-D-xylopyranoside, obtained according to preparation I, and 2-furanboronic acid, the expected product is obtained and is reacted further without additional purification in order to obtain the nonacetylated xyloside.

Example 176

3-(2-Furyl)phenyl 5-thio-β-D-xylopyranoside

By carrying out the operation analogously to example 14, starting from the product obtained according to example 175, the expected compound is obtained in the form of a white powder with a yield of 30%.
M.p.=138° C.
$[\alpha]_D^{28}=-96°$ (c=0.22; CH$_3$OH).

Example 177

3-(2-Methoxy-5-pyrimidinyl)phenyl 2,3,4-tri-O-acetyl-5-thio-β-D-xylopyranoside

By carrying out the operation analogously to example 3, starting from 3-bromophenyl 2,3,4-tri-O-acetyl-5-thio-β-D-xylopyranoside, obtained according to preparation VII, and 2-methoxy-5-pyrimidineboronic acid, the expected product is obtained and is reacted further without additional purification in order to obtain the nonacetylated xyloside.

Example 178

3-(2-Methoxy-5-pyrimidinyl)phenyl 5-thio-β-D-xylopyranoside

By carrying out the operation analogously to example 4, starting from the product obtained according to example 177, the expected compound is obtained in the form of a white solid with a yield of 69%.
M.p.=171° C.
$[\alpha]_D^{30}=-76°$ (c=0.12; DMSO).

Example 179

4-Chloro-2-(5-isoxazolyl)-5-methylphenyl 2,3,4-tri-O-acetyl-5-thio-β-D-xylopyranoside A mixture of 0.8 g (5.87 mmol) of zinc chloride, 2 g of 13× molecular sieve, 2 g (5.6 mmol) of 2,3,4-tri-O-acetyl-5-thio-α-D-xylopyranosyl bromide, 1 g (4.77 mmol) of 4-chloro-2-(5-isoxazolyl)-5-methylphenol, 1 g (5.7 mmol) of silver imidazolate, 5 ml of toluene and 5 ml of acetonitrile is prepared. The mixture is kept stirred at 80° C. for 90 minutes and then cooled and filtered. The residual solid is rinsed on the filter with methanol and the combined filtrates are concentrated under reduced pressure. The crude product obtained is purified by chromatography on silica gel, elution being carried out using a dichloromethane/ethyl acetate mixture (9/1; v/v). The pure fraction is crystallized from ethyl ether. The expected compound is thus obtained in the form of a white solid with a yield of 10%.
M.p.=203° C.
$[\alpha]_D^{28}=-49°$ (c=0.18; DMSO).

Example 180

4-Chloro-2-(5-isoxazolyl)-5-methylphenyl 5-thio-β-D-xylopyranoside

By carrying out the operation analogously to example 14, starting from the product obtained according to example 179, the expected compound is obtained in the form of a white solid with a yield of 45%.
M.p.=239° C.
$[\alpha]_D^{29}=-78°$ (c=0.17; DMSO).

Example 181

4-Chloro-5-methyl-2-(1-phenyl-1H-pyrazol-5-yl)phenyl 2,3,4-tri-O-acetyl-5-thio-β-D-xylopyranoside By carrying out the operation analogously to example 179, starting from 4-chloro-5-methyl-2-(1-phenyl-1H-pyrazol-5-yl)phenol, the expected product is obtained and is reacted further without additional purification in order to obtain the nonacetylated xyloside.

Example 182

4-Chloro-5-methyl-2-(1-phenyl-1H-pyrazol-5-yl)phenyl 5-thio-β-D-xylopyranoside

By carrying out the operation analogously to example 14, starting from the product obtained according to example 181, the expected compound is obtained in the form of a white solid with a yield of 2%.
M.p.=95-99° C.
$[\alpha]_D^{27}=-109°$ (c=0.22; DMSO).

Example 183

2-(5-Isoxazolyl)phenyl 2,3,4-tri-O-acetyl-5-thio-β-D-xylopyranoside

By carrying out the operation analogously to preparation I, starting from 2-(5-isoxazolyl)phenol, the expected compound is obtained in the form of a white solid with a yield of 18%.
M.p.=75° C.
$[\alpha]_D^{26}=-92°$ (c=0.22; DMSO).

Example 184

2-(5-Isoxazolyl)phenyl 5-thio-β-D-xylopyranoside

By carrying out the operation analogously to example 4, starting from the product obtained according to example 183, the expected compound is obtained in the form of a white solid with a yield of 70%.

M.p.=200° C.
$[\alpha]_D^{25}$=−106° (c=0.24; DMSO).

Example 185

2-(1H-Indol-1-yl)phenyl 2,3,4-tri-O-acetyl-5-thio-β-D-xylopyranoside

By carrying out the operation analogously to preparation I, starting from 2-(1H-indol-1-yl)phenol, the expected product is obtained and is reacted further without additional purification in order to obtain the nonacetylated xyloside.

Example 186

2-(1H-Indol-1-yl)phenyl 5-thio-β-D-xylopyranoside

By carrying out the operation analogously to example 4, starting from the product obtained according to example 185, the expected compound is obtained in the form of a white solid with a yield of 10%.
M.p.=70-73° C.
$[\alpha]_D^{29}$=−79° (c=0.22; DMSO).

Example 187

2-(2-Benzothiazolyl)phenyl 2,3,4-tri-O-acetyl-5-thio-β-D-xylopyranoside

A solution of 2.19 g (7.5 mmol) of 2,3,4-tri-O-acetyl-5-thio-D-xylopyranose in 30 ml of THF is prepared and 1.136 g (5 mmol) of 2-(2-benzothiazolyl)phenol, 1.97 g (7.5 mmol) of triphenylphosphine and 1.52 g (7.5 mmol) of diisopropyl azodicarboxylate are added at 0° C. The reaction mixture is stirred at 0° C. for 1 hour and then at ambient temperature for 4 hours, and filtered. The filtrate is concentrated under reduced pressure and the crude product obtained is purified by chromatography on silica gel, elution being carried out using a toluene/isopropanol mixture (98/2; v/v). The pure fraction is crystallized from an ethyl acetate/ethyl ether mixture. The expected compound is thus obtained in the form of a white solid with a yield of 32%.
M.p.=168° C.
$[\alpha]_D^{29}$=−81° (c=0.25; DMSO).

Example 188

2-(2-Benzothiazolyl)phenyl 5-thio-β-D-xylopyranoside

By carrying out the operation analogously to example 4, starting from the product obtained according to example 187, the expected compound is obtained in the form of a white solid with a yield of 60%.
M.p.=196° C.
$[\alpha]_D^{29}$=−47° (c=0.21; DMSO).

Example 189

4-(1H-Imidazol-1-yl)phenyl 2,3,4-tri-O-acetyl-5-thio-β-D-xylopyranoside

A mixture of 3 g (22 mmol) of zinc chloride, 5 g of 4 Å molecular sieve, 6.5 g of zinc oxide, 9 g (25 mmol) of 2,3,4-tri-O-acetyl-5-thio-β-D-xylopyranosyl bromide, 3.2 g (20 mmol) of 4-(1H-imidazol-1-yl)phenol, 70 ml of toluene and 70 ml of acetonitrile is prepared. The mixture is kept stirred at 55° C. for 24 hours and then cooled and filtered. The residual solid is rinsed on the filter with ethyl acetate and the combined filtrates are successively washed with water, with an N sodium hydroxide solution and again with water to neutral pH. The organic phase is subsequently dried over magnesium sulfate and concentrated under reduced pressure. The crude product obtained is purified by chromatography on silica gel, elution being carried out using an ethyl acetate/ethyl ether mixture (8/5; v/v). The expected compound is thus obtained in the form of a pulverulent solid which is reacted further in order to obtain the nonacetylated xyloside.

Example 190

4-(1H-Imidazol-1-yl)phenyl 5-thio-β-D-xylopyranoside

By carrying out the operation analogously to example 14, starting from the product obtained according to example 189, the expected compound is obtained in the form of a fluffy white solid with a yield of 5%.
M.p.=180° C.
$[\alpha]_D^{22}$=−62° (c=0.30; DMSO).

Example 191

3-(3-Methyl-2-pyridinyl)phenyl 5-thio-β-D-xylopyranoside

By carrying out the operation analogously to example 29, starting from 3-methyl-2-pyridineboronic acid, the expected compound is obtained in the form of a light grey solid with a yield of 23%.
M.p.=97-109° C.
$[\alpha]_D^{29}$=−50° (c=0.34; DMSO).

Example 192

3-(4-Methoxy-3-pyridinyl)phenyl 5-thio-β-D-xylopyranoside

By carrying out the operation analogously to example 29, starting from 4-methoxy-3-pyridineboronic acid, the expected compound is obtained in the form of a white solid with a yield of 8%.
M.p.=195° C.
$[\alpha]_{27}$=−52° (c=0.22; DMSO).

Example 193

3-(2-Chloro-4-pyridinyl)phenyl 5-thio-β-D-xylopyranoside

By carrying out the operation analogously to example 29, starting from 2-chloro-4-pyridineboronic acid, the expected compound is obtained in the form of a white powder with a yield of 14%.
M.p.=207° C. (crystallized from a water/isopropanol mixture).
$[\alpha]_D^{29}$=−79° (c=0.26; DMSO).

Example 194

3-(2-Methyl-4-pyridinyl)phenyl 5-thio-β-D-xylopyranoside

By carrying out the operation analogously to example 29, starting from 2-methyl-4-pyridineboronic acid, the expected compound is obtained in the form of a white powder with a yield of 50%.

M.p.=223° C.
[α]$_D^{28}$=−76° (c=0.39; DMSO).

Example 195

3-(5-pyrimidinyl)phenyl 5-thio-β-D-xylopyranoside

By carrying out the operation analogously to example 29, starting from 5-pyrimidineboronic acid, the expected compound is obtained in the form of white crystals with a yield of 46%.
M.p.=241° C. (crystallized from water).
[α]$_D^{25}$=−87° (c=0.12; DMSO).

Example 196

3-(2-Pyrimidinyl)phenyl 5-thio-β-D-xylopyranoside

By carrying out the operation analogously to example 29, starting from 2-pyrimidineboronic acid, the expected compound is obtained in the form of a beige solid with a yield of 33%.
M.p.=164-166° C.
[α]$_D^{26}$=−69° (c=0.28; DMSO).

Example 197

3-(3-Furyl)phenyl 5-thio-β-D-xylopyranoside

By carrying out the operation analogously to example 29, starting from 3-furanboronic acid, the expected compound is obtained in the form of a white powder with a yield of 65%.
M.p.=152° C.
[α]$_D^{27}$=−73° (c=0.15; MeOH).

Example 198

2-(3-Furyl)phenyl 5-thio-β-D-xylopyranoside

By carrying out the operation analogously to example 29, starting from 2-bromophenyl 2,3,4-tri-O-acetyl-5-thio-β-D-xylopyranoside, obtained according to preparation IV, and 3-furanboronic acid, the expected compound is obtained in the form of white flakes with a yield of 57%.
M.p.=102° C.
[α]$_D^{32}$=−107° (c=0.16; MeOH).

Example 199

4-(3,5-Dimethyl-4-isoxazolyl)phenyl 5-thio-β-D-xylopyranoside

By carrying out the operation analogously to example 29, starting from 4-iodophenyl 2,3,4-tri-O-acetyl-5-thio-β-D-xylopyranoside, obtained according to preparation II, and 3,5-dimethyl-4-isoxazoleboronic acid, the expected compound is obtained in the form of a white solid with a yield of 63%.
M.p.=175-179° C.
[α]$_D^{30}$=−56° (c=0.26; DMSO).

Example 200

4-(5-Pyrimidinyl)phenyl 5-thio-β-D-xylopyranoside

By carrying out the operation analogously to example 199, starting from 5-pyrimidineboronic acid, the expected compound is obtained in the form of a white solid with a yield of 55%.
M.p.=196-200° C.
[α]$_D^{31}$=−34° (c=0.13; DMSO).

Example 201

4-(3-Furyl)phenyl 5-thio-β-D-xylopyranoside

By carrying out the operation analogously to example 199, starting from 3-furanboronic acid, the expected compound is obtained in the form of white flakes with a yield of 84%.
M.p.=194° C.
[α]$_D^{31}$=−197° (c=0.30; CH$_3$OH).

Example 202

2,3-Difluoro-5-(6-cyano-3-pyridinyl)phenyl 2,3,4-tri-O-acetyl-5-thio-β-D-xylopyranoside By carrying out the operation analogously to example 97, starting from the compound obtained according to preparation VIII and 2-cyano-5-(pinacolatoboryl)pyridine, the expected product is obtained and is reacted further without additional purification in order to obtain the nonacetylated xyloside.

Example 203

2,3-Difluoro-5-(6-cyano-3-pyridinyl)phenyl 5-thio-β-D-xylopyranoside

By carrying out the operation analogously to example 4, starting from the product obtained according to example 202, the expected compound is obtained in the form of a white solid with a yield of 33%.
M.p.=173° C.
[α]$_D^{31}$=−71° (c=0.10; DMSO).

Example 204

2-Chloro-5-(6-cyano-3-pyridinyl)phenyl 2,3,4-tri-O-acetyl-5-thio-β-D-xylopyranoside By carrying out the operation analogously to example 202, starting from the compound obtained according to preparation X, the expected product is obtained and is reacted further without additional purification in order to obtain the nonacetylated xyloside.

Example 205

2-Chloro-5-(6-cyano-3-pyridinyl)phenyl 5-thio-β-D-xylopyranoside

By carrying out the operation analogously to example 4, starting from the product obtained according to example 204, the expected compound is obtained in the form of a white solid with a yield of 8%.
M.p.=192° C.
[α]$_D^{30}$=−28° (c=0.10; DMSO).

The structures of the compounds of formula I described above are shown in the following table:

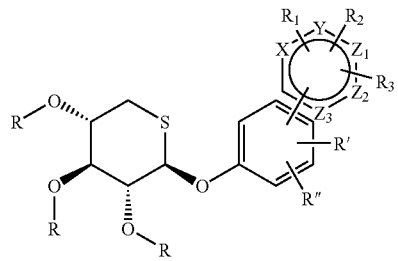

Table of Examples

| Ex. | R' | R" | Pos A | Pos X | X | Y | Z1 | Z2 | Z3 | R1 | R2 | R3 | R |
|---|---|---|---|---|---|---|---|---|---|---|---|---|---|
| 1 | H | H | 3 | 4 | N | C | C | C | C | H | H | H | Ac |
| 2 | H | H | 3 | 4 | N | C | C | C | C | H | H | H | H |
| 3 | 5-F | H | 2 | 3 | N | C | C | C | C | H | H | H | Ac |
| 4 | 5-F | H | 2 | 3 | N | C | C | C | C | H | H | H | H |
| 5 | H | H | 4 | 3 | N | C | C | C | C | H | H | H | Ac |
| 6 | H | H | 4 | 3 | N | C | C | C | C | H | H | H | H |
| 7 | H | H | 4 | 4 | N | C | C | C | C | H | H | H | Ac |
| 8 | H | H | 4 | 4 | N | C | C | C | C | H | H | H | H |
| 9 | H | H | 4 | 2 | N | C | C | C | C | H | H | H | Ac |
| 10 | H | H | 4 | 2 | N | C | C | C | C | H | H | H | H |
| 11 | H | H | 3 | 2 | N | C | C | C | C | H | H | H | Ac |
| 12 | H | H | 3 | 2 | N | C | C | C | C | H | H | H | H |
| 13 | 3-CH$_3$ | 5-CH$_3$ | 4 | 4 | N | C | C | C | C | H | H | H | Ac |
| 14 | 3-CH$_3$ | 5-CH$_3$ | 4 | 4 | N | C | C | C | C | H | H | H | H |
| 15 | H | H | 2 | 4 | N | C | C | C | C | H | H | H | Ac |
| 16 | H | H | 2 | 4 | N | C | C | C | C | H | H | H | H |
| 17 | H | H | 2 | 3 | N | C | C | C | C | H | H | H | Ac |
| 18 | H | H | 2 | 3 | N | C | C | C | C | H | H | H | H |
| 19 | 3-CH$_3$ | 5-CH$_3$ | 4 | 3 | N | C | C | C | C | H | H | H | Ac |
| 20 | 3-CH$_3$ | 5-CH$_3$ | 4 | 3 | N | C | C | C | C | H | H | H | H |
| 21 | H | H | 3 | 3 | N | C | C | C | C | H | H | H | Ac |
| 22 | H | H | 3 | 3 | N | C | C | C | C | H | H | H | H |
| 23 | 2-F | H | 4 | 3 | N | C | C | C | C | H | H | H | Ac |
| 24 | 2-F | H | 4 | 3 | N | C | C | C | C | H | H | H | H |
| 25 | 2-F | H | 4 | 4 | N | C | C | C | C | H | H | H | Ac |
| 26 | 2-F | H | 4 | 4 | N | C | C | C | C | H | H | H | H |
| 27 | 5-F | H | 2 | 4 | N | C | C | C | C | H | H | H | Ac |
| 28 | 5-F | H | 2 | 4 | N | C | C | C | C | H | H | H | H |
| 29 | H | H | 3 | 3 | N | C | C | C | C | 6-CH$_3$ | H | H | H |
| 30 | H | H | 3 | 3 | N | C | C | C | C | 6-F | H | H | Ac |
| 31 | H | H | 3 | 3 | N | C | C | C | C | 6-F | H | H | H |
| 32 | H | H | 3 | 3 | N | C | C | C | C | 2-OCH$_3$ | H | H | Ac |
| 33 | H | H | 3 | 3 | N | C | C | C | C | 2-OCH$_3$ | H | H | H |
| 34 | H | H | 3 | 3 | N | C | C | C | C | 6-CN | H | H | Ac |
| 35 | H | H | 3 | 3 | N | C | C | C | C | 6-CN | H | H | H |
| 36 | H | H | 3 | 3 | N | C | C | C | C | 4-CH$_3$ | H | H | Ac |
| 37 | H | H | 3 | 3 | N | C | C | C | C | 4-CH$_3$ | H | H | H |
| 38 | H | H | 3 | 3 | N | C | C | C | C | 5-OCH$_3$ | H | H | Ac |
| 39 | H | H | 3 | 3 | N | C | C | C | C | 5-OCH$_3$ | H | H | H |
| 40 | H | H | 3 | 3 | N | C | C | C | C | 2-CH$_3$ | H | H | Ac |
| 41 | H | H | 3 | 3 | N | C | C | C | C | 2-CH$_3$ | H | H | H |
| 42 | H | H | 3 | 3 | N | C | C | C | C | 5-CH$_3$ | H | H | Ac |
| 43 | H | H | 3 | 3 | N | C | C | C | C | 5-CH$_3$ | H | H | H |
| 44 | H | H | 3 | 2 | N | C | C | C | C | 3-F | H | H | Ac |
| 45 | H | H | 3 | 2 | N | C | C | C | C | 3-F | H | H | H |
| 46 | H | H | 3 | 2 | N | C | C | C | C | 6-OCH$_3$ | H | H | Ac |
| 47 | H | H | 3 | 2 | N | C | C | C | C | 6-OCH$_3$ | H | H | H |
| 48 | H | H | 3 | 5 | S | sb | C | N | C | 2-CH$_3$ | 4-CH$_3$ | — | Ac |
| 49 | H | H | 3 | 5 | S | sb | C | N | C | 2-CH$_3$ | 4-CH$_3$ | — | H |
| 50 | H | H | 3 | 2 | N | C | C | C | C | 4-Cl | H | H | Ac |
| 51 | H | H | 3 | 2 | N | C | C | C | C | 4-Cl | H | H | H |
| 52 | H | H | 3 | 2 | N | C | C | C | C | 5-CH$_3$ | H | H | Ac |
| 53 | H | H | 3 | 2 | N | C | C | C | C | 5-CH$_3$ | H | H | H |
| 54 | H | H | 3 | 2 | N | C | C | C | C | 6-Cl | H | H | Ac |

-continued

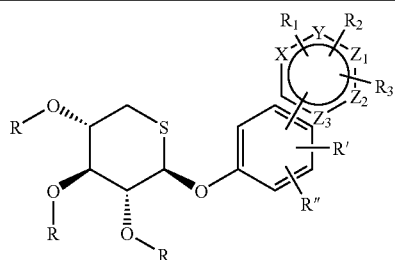

Table of Examples

| Ex. | R' | R" | Pos A | Pos X | X | Y | Z1 | Z2 | Z3 | R1 | R2 | R3 | R |
|---|---|---|---|---|---|---|---|---|---|---|---|---|---|
| 55 | H | H | 3 | 2 | N | C | C | C | C | 6-Cl | H | H | H |
| 56 | H | H | 3 | 2 | N | C | C | N | C | H | H | H | Ac |
| 57 | H | H | 3 | 2 | N | C | C | N | C | H | H | H | H |
| 58 | H | H | 3 | 3 | N | C | C | C | C | 6-OH | H | H | Ac |
| 59 | H | H | 3 | 3 | N | C | C | C | C | 6-OH | H | H | H |
| 60 | H | H | 3 | 4 | N | sb | N | C | C | 1-CH₃ | 3-CF₃ | 5-H | Ac |
| 61 | H | H | 3 | 4 | N | sb | N | C | C | 3-CH₃ | 3-CF₃ | 5-H | H |
| 62 | H | H | 3 | 4 | N | sb | N | C | C | 5-CH₃ | 3-CF₃ | 1-H | Ac |
| 63 | H | H | 3 | 4 | N | sb | N | C | C | 5-CH₃ | 3-CF₃ | 1-H | H |
| 64 | H | H | 3 | 2 | S | sb | C | N | C | H | H | — | Ac |
| 65 | H | H | 3 | 2 | S | sb | C | N | C | H | H | — | H |
| 66 | H | H | 3 | 2 | N | C | C | C | C | 5-F | H | H | Ac |
| 67 | H | H | 3 | 2 | N | C | C | C | C | 5-F | H | H | H |
| 68 | H | H | 3 | 2 | N | C | C | C | C | 3-Cl | H | H | Ac |
| 69 | H | H | 3 | 2 | N | C | C | C | C | 3-Cl | H | H | H |
| 70 | H | H | 3 | 4 | O | sb | N | C | C | 5-CH₃ | 3-H | — | Ac |
| 71 | H | H | 3 | 4 | O | sb | N | C | C | 5-CH₃ | 3-H | — | H |
| 72 | H | H | 3 | 2 | N | C | C | C | C | 4-CH₃ | H | H | Ac |
| 73 | H | H | 3 | 2 | N | C | C | C | C | 4-CH₃ | H | H | H |
| 74 | H | H | 3 | 3 | N | C | C | C | C | 6-N(Me)₂ | H | H | Ac |
| 75 | H | H | 3 | 3 | N | C | C | C | C | 6-N(Me)₂ | H | H | H |
| 76* | H | H | 3 | 3 | N | C | C | C | C | 6-N(Me)₂ | H | H | H |
| 77 | 2-Cl | H | 5 | 4 | O | sb | N | C | C | 3-CH₃ | 5-CH₃ | — | Ac |
| 78 | 2-Cl | H | 5 | 4 | O | sb | N | C | C | 3-CH₃ | 5-CH₃ | — | H |
| 79 | 2-Cl | H | 5 | 4 | O | sb | N | C | C | 5-CH₃ | H | — | Ac |
| 80 | 2-Cl | H | 5 | 4 | O | sb | N | C | C | 5-CH₃ | H | — | H |
| 81 | 2-Cl | H | 5 | 2 | N | C | C | C | C | H | H | H | Ac |
| 82 | 2-Cl | H | 5 | 2 | N | C | C | C | C | H | H | H | H |
| 83 | 2-F | 3-F | 5 | 2 | N | C | C | C | C | H | H | H | Ac |
| 84 | 2-F | 3-F | 5 | 2 | N | C | C | C | C | H | H | H | H |
| 85 | H | H | 3 | 2 | N | C | C | C | C | 6-CH₃ | H | H | Ac |
| 86 | H | H | 3 | 2 | N | C | C | C | C | 6-CH₃ | H | H | H |
| 87 | H | H | 3 | 4 | N | sb | N | C | C | 1-CH₃ | 3-CH₃ | 5-CH₃ | Ac |
| 88 | H | H | 3 | 4 | N | sb | N | C | C | 1-CH₃ | 3-CH₃ | 5-CH₃ | H |
| 89 | H | H | 3 | 3 | N | C | C | C | C | 5-Cl | H | H | Ac |
| 90 | H | H | 3 | 3 | N | C | C | C | C | 5-Cl | H | H | H |
| 91 | H | H | 3 | 3 | N | C | C | C | C | 5-F | H | H | Ac |
| 92 | H | H | 3 | 3 | N | C | C | C | C | 5-F | H | H | H |
| 93 | H | H | 3 | 4 | N | sb | N | C | C | 1-CH₃ | 3-H | 5-H | Ac |
| 94 | H | H | 3 | 4 | N | sb | N | C | C | 1-CH₃ | 3-H | 5-H | H |
| 95 | H | H | 3 | 4 | N | sb | N | C | C | 1-H | 3-CH₂ | 5-CH₃ | Ac |
| 96 | H | H | 3 | 4 | N | sb | N | C | C | 1-H | 3-CH₂ | 5-CH₃ | H |
| 97 | 2-Cl | H | 5 | 4 | N | sb | N | C | C | 1-CH₃ | 3-H | 5-H | Ac |
| 98 | 2-Cl | H | 5 | 4 | N | sb | N | C | C | 1-CH₃ | 3-H | 5-H | H |
| 99 | 2-F | 3-F | 5 | 4 | N | sb | N | C | C | 1-CH₃ | 3-H | 5-H | Ac |
| 100 | 2-F | 3-F | 5 | 4 | N | sb | N | C | C | 1-CH₃ | 3-H | 5-H | H |
| 101 | 2-Cl | H | 5 | 3 | N | C | C | C | C | H | H | H | Ac |
| 102 | 2-Cl | H | 5 | 3 | N | C | C | C | C | H | H | H | H |
| 103 | 4-Cl | H | 3 | 3 | N | C | C | C | C | H | H | H | Ac |
| 104 | 4-Cl | H | 3 | 3 | N | C | C | C | C | H | H | H | H |
| 105 | 2-F | 3-F | 5 | 3 | N | C | C | C | C | H | H | H | Ac |
| 106 | 2-F | 3-F | 5 | 3 | N | C | C | C | C | H | H | H | H |
| 107 | 2-F | H | 5 | 3 | N | C | C | C | C | H | H | H | Ac |
| 108 | 2-F | H | 5 | 3 | N | C | C | C | C | H | H | H | H |
| 109 | H | H | 3 | 4 | N | C | C | C | C | 2-F | H | H | Ac |
| 110 | H | H | 3 | 4 | N | C | C | C | C | 2-F | H | H | H |
| 111 | H | H | 3 | 4 | N | C | C | C | C | 3-Cl | H | H | Ac |
| 112 | H | H | 3 | 4 | N | C | C | C | C | 3-Cl | H | H | H |
| 113 | H | H | 3 | 3 | N | C | C | C | C | 2-Cl | H | H | Ac |

-continued

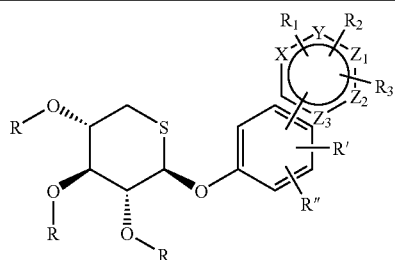

Table of Examples

| Ex. | R' | R" | Pos A | Pos X | X | Y | Z1 | Z2 | Z3 | R1 | R2 | R3 | R |
|---|---|---|---|---|---|---|---|---|---|---|---|---|---|
| 114 | H | H | 3 | 3 | N | C | C | C | C | 2-Cl | H | H | H |
| 115 | H | H | 3 | 2 | S | sb | C | C | C | H | H | H | Ac |
| 116 | H | H | 3 | 2 | S | sb | C | C | C | H | H | H | H |
| 117 | H | H | 3 | 3 | N | C | C | C | C | 2-F | H | H | Ac |
| 118 | H | H | 3 | 3 | N | C | C | C | C | 2-F | H | H | H |
| 119 | H | H | 3 | 3 | S | sb | C | C | C | H | H | H | Ac |
| 120 | H | H | 3 | 3 | S | sb | C | C | C | H | H | H | H |
| 121 | H | H | 3 | 2 | O | sb | C | C | C | 5-CH$_3$ | H | H | Ac |
| 122 | H | H | 3 | 2 | O | sb | C | C | C | 5-CH$_3$ | H | H | H |
| 123 | H | H | 3 | 3 | N | C | C | C | C | 6-Cl | H | H | Ac |
| 124 | H | H | 3 | 3 | N | C | C | C | C | 6-Cl | H | H | H |
| 125 | H | H | 3 | 3 | N | C | C | C | C | 6-OMe | H | H | Ac |
| 126 | H | H | 3 | 3 | N | C | C | C | C | 6-OMe | H | H | H |
| 127 | H | H | 3 | 4 | O | sb | N | C | C | 3-CH$_3$ | 5-CH$_3$ | — | Ac |
| 128 | H | H | 3 | 4 | O | sb | N | C | C | 3-CH$_3$ | 5-CH$_3$ | — | H |
| 129 | 2-F | 3-F | 5 | 4 | N | C | C | C | C | H | H | H | Ac |
| 130 | 2-F | 3-F | 5 | 4 | N | C | C | C | C | H | H | H | H |
| 131 | 2-F | 3-F | 5 | 4 | O | sb | N | C | C | 3-CH$_3$ | 5-CH$_3$ | — | Ac |
| 132 | 2-F | 3-F | 5 | 4 | O | sb | N | C | C | 3-CH$_3$ | 5-CH$_3$ | — | H |
| 133 | 2-F | 3-F | 5 | 3 | N | C | C | C | C | 6-CH$_3$ | H | H | Ac |
| 134 | 2-F | 3-F | 5 | 3 | N | C | C | C | C | 6-CH$_3$ | H | H | H |
| 135 | 2-F | 3-F | 5 | 4 | N | C | C | C | C | 2-CH$_3$ | H | H | Ac |
| 136 | 2-F | 3-F | 5 | 4 | N | C | C | C | C | 2-CH$_3$ | H | H | H |
| 137 | 2-F | 3-F | 5 | 3 | N | C | C | C | C | 2-OMe | H | H | Ac |
| 138 | 2-F | 3-F | 5 | 3 | N | C | C | C | C | 2-OMe | H | H | H |
| 139 | 2-F | 3-F | 5 | 3 | N | C | C | C | C | 2-F | H | H | Ac |
| 140 | 2-F | 3-F | 5 | 3 | N | C | C | C | C | 2-F | H | H | H |
| 141 | 2-F | 3-F | 5 | 5 | N | C | C | C | C | H | H | H | Ac |
| 142 | 2-F | 3-F | 5 | 5 | N | C | C | C | C | H | H | H | H |
| 143 | 2-F | 3-F | 5 | 4 | N | C | C | C | C | 2-F | H | H | Ac |
| 144 | 2-F | 3-F | 5 | 4 | N | C | C | C | C | 2-F | H | H | H |
| 145 | 2-F | 3-F | 5 | 3 | N | C | C | C | C | 6-F | H | H | Ac |
| 146 | 2-F | 3-F | 5 | 3 | N | C | C | C | C | 6-F | H | H | H |
| 147 | H | H | 2 | 4 | O | sb | N | C | C | 3-CH$_3$ | 5-CH$_3$ | — | Ac |
| 148 | H | H | 2 | 4 | O | sb | N | C | C | 3-CH$_3$ | 5-CH$_3$ | — | H |
| 149 | 2-F | H | 4 | 4 | O | sb | N | C | C | 3-CH$_3$ | 5-CH$_3$ | — | Ac |
| 150 | 2-F | H | 4 | 4 | O | sb | N | C | C | 3-CH$_3$ | 5-CH$_3$ | — | H |
| 151 | 2-F | H | 4 | 3 | O | sb | N | C | C | H | H | H | Ac |
| 152 | 2-F | H | 4 | 3 | O | sb | N | C | C | H | H | H | H |
| 153 | 5-F | H | 2 | 3 | O | sb | N | C | C | H | H | H | Ac |
| 154 | 5-F | H | 2 | 3 | O | sb | N | C | C | H | H | H | H |
| 155 | 5-F | H | 2 | 4 | O | sb | N | C | C | 3-CH$_3$ | 5-CH$_3$ | — | Ac |
| 156 | 5-F | H | 2 | 4 | O | sb | N | C | C | 3-CH$_3$ | 5-CH$_3$ | — | H |
| 157 | 2-Cl | H | 5 | 4 | N | C | C | C | C | 2-CH$_3$ | H | H | Ac |
| 158 | 2-Cl | H | 5 | 4 | N | C | C | C | C | 2-CH$_3$ | H | H | H |
| 159 | 2-Cl | H | 5 | 3 | N | C | C | C | C | 6-CH$_3$ | H | H | Ac |
| 160 | 2-Cl | H | 5 | 3 | N | C | C | C | C | 6-CH$_3$ | H | H | H |
| 161 | 2-Cl | H | 5 | 3 | N | C | C | C | C | 2-OMe | H | H | Ac |
| 162 | 2-Cl | H | 5 | 3 | N | C | C | C | C | 2-OMe | H | H | H |
| 163 | 2-Cl | H | 5 | 4 | N | C | C | C | C | 2-F | H | H | Ac |
| 164 | 2-Cl | H | 5 | 4 | N | C | C | C | C | 2-F | H | H | H |
| 165 | 2-Cl | H | 5 | 3 | N | C | C | C | C | 2-F | H | H | Ac |
| 166 | 2-Cl | H | 5 | 3 | N | C | C | C | C | 2-F | H | H | H |
| 167 | 2-Cl | H | 5 | 4 | N | C | C | C | C | H | H | H | Ac |
| 168 | 2-Cl | H | 5 | 4 | N | C | C | C | C | H | H | H | H |
| 169 | 2-Cl | H | 5 | 5 | N | C | N | C | C | H | H | H | Ac |
| 170 | 2-Cl | H | 5 | 5 | N | C | N | C | C | H | H | H | H |
| 171 | 2-Cl | H | 5 | 3 | N | C | C | C | C | 6-F | H | H | Ac |
| 172 | 2-Cl | H | 5 | 3 | N | C | C | C | C | 6-F | H | H | H |
| 173 | H | H | 4 | 2 | O | sb | C | C | C | H | H | H | Ac |
| 174 | H | H | 4 | 2 | O | sb | C | C | C | H | H | H | H |
| 175 | H | H | 3 | 2 | O | sb | C | C | C | H | H | H | Ac |

-continued

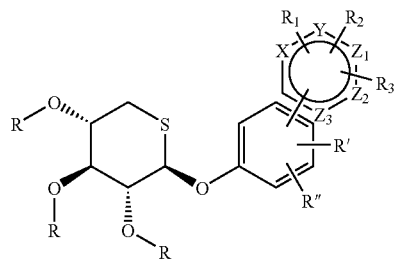

Table of Examples

| Ex. | R' | R" | Pos A | Pos X | X | Y | Z1 | Z2 | Z3 | R1 | R2 | R3 | R |
|---|---|---|---|---|---|---|---|---|---|---|---|---|---|
| 176 | H | H | 3 | 2 | O | sb | C | C | C | H | H | H | H |
| 177 | H | H | 3 | 5 | N | C | N | C | C | 2-OMe | H | H | Ac |
| 178 | H | H | 3 | 5 | N | C | N | C | C | 2-OMe | H | H | H |
| 179 | 4-Cl | 5-CH₃ | 2 | 5 | O | sb | N | C | C | H | H | — | Ac |
| 180 | 4-Cl | 5-CH₃ | 2 | 5 | O | sb | N | C | C | H | H | — | H |
| 181 | 4-Cl | 5-CH₃ | 2 | 5 | N | sb | N | C | C | 1-Ph | H | H | Ac |
| 182 | 4-Cl | 5-CH₃ | 2 | 5 | N | sb | N | C | C | 1-Ph | H | H | H |
| 183 | H | H | 2 | 5 | O | sb | N | C | C | H | H | — | Ac |
| 184 | H | H | 2 | 5 | O | sb | N | C | C | H | H | — | H |
| 185 | H | H | 2 | 1 | N | sb | N | C | C | 2-¤ | 3-¤ | H | Ac |
| 186 | H | H | 2 | 1 | N | sb | N | C | C | 2-¤ | 3-¤ | H | H |
| 187 | H | H | 2 | 2 | S | sb | C | N | C | 4-¤ | 5-¤ | — | Ac |
| 188 | H | H | 2 | 2 | S | sb | C | N | C | 4-¤ | 5-¤ | — | H |
| 189 | H | H | 4 | 1 | N | sb | C | N | C | H | H | H | Ac |
| 190 | H | H | 4 | 1 | N | sb | C | N | C | H | H | H | H |
| 191 | H | H | 3 | 2 | N | C | C | C | C | 3-CH₃ | H | H | H |
| 192 | H | H | 3 | 3 | N | C | C | C | C | 4-OMe | H | H | H |
| 193 | H | H | 3 | 4 | N | C | C | C | C | 2-Cl | H | H | H |
| 194 | H | H | 3 | 4 | N | C | C | C | C | 2-CH₃ | H | H | H |
| 195 | H | H | 3 | 5 | N | C | N | C | C | H | H | H | H |
| 196 | H | H | 3 | 2 | N | C | N | C | C | H | H | H | H |
| 197 | H | H | 3 | 3 | O | sb | C | C | C | H | H | H | H |
| 198 | H | H | 2 | 3 | O | sb | C | C | C | H | H | H | H |
| 199 | H | H | 4 | 4 | O | sb | N | C | C | 3-CH₃ | 5-CH₃ | H | H |
| 200 | H | H | 4 | 5 | N | C | N | C | C | H | H | H | H |
| 201 | H | H | 4 | 3 | O | sb | C | C | C | H | H | H | H |
| 202 | 2-F | 3-F | 5 | 3 | N | C | C | C | C | 6-CN | H | H | Ac |
| 203 | 2-F | 3-F | 5 | 3 | N | C | C | C | C | 6-CN | H | H | H |
| 204 | 2-Cl | H | 5 | 3 | N | C | C | C | C | 6-CN | H | H | Ac |
| 205 | 2-Cl | H | 5 | 3 | N | C | C | C | C | 6-CN | H | H | H |

*hydrochloride

In the foregoing table:

the positions of R' and R" are indicated with respect to the position 1 of the 5-thio-β-D-xylopyranoside group on the phenyl ring, Pos-A indicates the position of the heterocycle A with respect to the position 1 of the 5-thio-β-D-xylopyranoside group, X indicates the nature of the primary heteroatom of the heterocycle A and its position with respect to the bond of the heterocycle A with the phenyl ring, "sb" means single bond, for the R1, R2 and R3 substituents, the figure indicates the position of the substituent on the heterocycle A with respect to the heteroatom X, x-¤ and y-¤ mean that R1 and R2 form, together with the atoms of the heterocycle to which they are attached, a benzene ring, A then representing a fused bicyclic heterocycle, Ac=COCH₃.

By way of example, Example 156 corresponds to the structure:

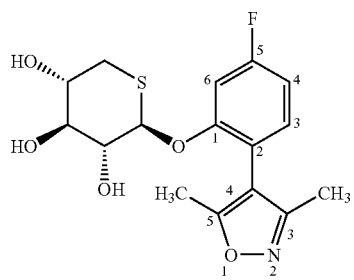

The antithrombotic activity of the compounds according to the invention was studied in vivo in rats by virtue of a test in which a venous thrombosis is reproduced.

The venous thrombosis was induced according to the protocol described in *Thromb. Haemost.*, 1992, 67(1), 176-179. The activity via the oral route was studied according to the procedure described below.

The experiment is carried out on non-fasting male Wistar rats weighing from 250 to 280 g and divided into groups of 10 animals each. The test products are administered orally (intubation) in solution or in suspension in a methylcellulose solution (0.5% in water). The concentrations of the compounds are calculated so as to bring about the absorption of an amount of solution of 10 ml/kg orally. A thrombosis is induced at time T after the administration of the product and the thrombus formed is removed and weighed. In order to induce this thrombosis, a venous stasis is brought about under hypercoagulation, according to the technique described by Wessler (*J. Applied Physiol.*, 1959, 943-946), using a solution of activated factor X (Xa), supplied by Biogenic (Montpellier) and comprising a dose of 7.5 nKat/kg, as hypercoagulant. The venous stasis is brought about 10 seconds exactly after the injection of the hypercoagulant. The activity of the test compounds was monitored at various doses, after they had been administered. The thrombosis was induced 2 hours after the administration of the compound. By way of example, the results of the above tests are given in the following table for a few compounds according to the invention (the activity is expressed by the percentage of inhibition of the formation of the thrombus, observed in the presence of the compound according to the invention, with respect to the weight of the thrombus formed in the absence of the compound).

TABLE I

Activity via the oral route

| Example | Dose (mg/kg) | Time (h) | Activity |
|---|---|---|---|
| 8 | 6 | 2 | 91 |
| 10 | 6 | 2 | 86 |
| 12 | 6 | 2 | 88 |
| 22 | 6 | 2 | 81 |
| 28 | 6 | 2 | 71 |

These results show that the compounds according to the invention exhibit an antithrombotic activity.

The present invention thus includes compounds of formula (I) according to the invention and their salts with an acid, solvates and hydrates which are pharmaceutically acceptable for their use as a medicament. The compound of formula (I) or one of its pharmaceutically acceptable salts, solvates or hydrates can be used in the preparation of an antithrombotic medicament intended in particular for the treatment or inhibition of disorders of the venous or arterial circulation and especially for correcting certain sensitive venous hematological parameters or for compensating for cardiac insufficiency. The compound of formula (I) or one of its pharmaceutically acceptable salts, solvates or hydrates can also be used in the preparation of a medicament intended for the inhibition of restenosis after transluminal arterial or coronary angioplasty or else to inhibit or treat pathologies of thromboembolic type which risk occurring subsequent, for example, to a surgical action, such as hip or knee arthroplasty. The compounds according to the invention can also be used as active substances of medicaments intended to inhibit strokes or heart attacks.

The present invention thus also includes pharmaceutical compositions comprising a compound of formula (I) or one of its pharmaceutically acceptable salts, solvates or hydrates. These pharmaceutical compositions generally comprise suitable excipients. Said excipients are chosen according to the pharmaceutical form desired and the method of administration desired, in particular oral or injectable.

These pharmaceutical compositions are prepared according to conventional methods well known to a person skilled in the art. For example, the compounds according to the invention can be formulated with physiologically acceptable excipients in order to obtain an injectable form to be used directly, an injectable form to be prepared at the time of use or a solid form for oral administration, such as, for example, a hard gelatin capsule or a tablet.

By way of example, an injectable form can be prepared preferably by lyophilization of a filtered and sterilized solution comprising the compound according to the invention and a soluble excipient in an amount necessary and sufficient to obtain an isotonic solution after addition at the time of use of water for injection. The solution obtained can be administered either in a single subcutaneous or intramuscular injection or in the form of a slow infusion. A form which can be administered orally will preferably be presented in the form of a hard gelatin capsule comprising the finely milled or better still micronized compound of the invention mixed with excipients known to a person skilled in the art, such as, for example, lactose, pregelatinized starch or magnesium stearate.

In order to obtain the desired therapeutic or prophylactic effect, each unit dose can comprise from 10 to 500 mg of at least one compound according to the invention.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A thioxylose compound selected from the group consisting of:
   a) compounds of formula I:

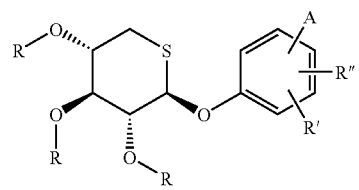

wherein:
   the pentapyranosyl group represents a 5-thio-β-D-xylopyranosyl group,
   R represents a hydrogen atom or a $C_2$-$C_6$ acyl group,
   R' and R" each independently represent a hydrogen atom, a halogen atom or a $C_1$-$C_4$ alkyl group, and
   A represents a 5- or 6-membered aromatic ring of formula:

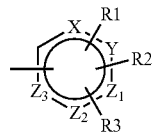

wherein:
   X represents a nitrogen, oxygen or sulfur atom,
   Y represents a carbon atom or a single bond,

63

Z₁, Z₂ and Z₃ each independently represent a carbon or nitrogen atom, and

R₁, R₂ and R₃ each independently represent a hydrogen atom, a halogen atom, a cyano group, a $C_1$-$C_4$ alkyl group, a hydroxyl group, a $C_1$-$C_4$ alkoxy group, a trifluoromethyl group or a dialkylamino group; or R₁ and R₂ together with the atoms of the heterocycle to which they are attached form an aromatic ring comprising 6 carbon atoms, whereby A represents a fused bicyclic group, b) addition salts thereof.

2. A compound as claimed in claim 1, wherein A represents a benzothiazolyl, benzofuranyl, indolyl or benzothienyl group.

3. A compound as claimed in claim 1, wherein the 5-thio-β-D-xylopyranosyl group and A are in the meta position relative to each other on the benzene ring.

4. A compound as claimed in claim 1, wherein the 5-thio-β-D-xylopyranosyl group and A are in the para position relative to each other on the benzene ring.

5. A compound as claimed in claim 1, wherein A represents a pyridine ring optionally substituted by at least one of the R₁, R₂ and R₃ groups as defined in claim 1.

6. A compound as claimed in claim 1, wherein R represents a hydrogen atom.

7. A compound as claimed in claim 1, wherein R represents a COCH₃ group.

8. A process for making a compound as claimed in claim 1, said process comprising:

a) reacting a starting compound of formula:

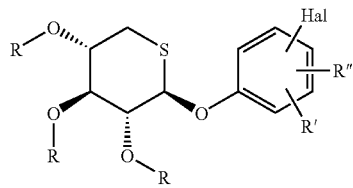

wherein:
Hal is a halogen atom,
R' and R" each independently represent a hydrogen atom, a halogen atom, or a $C_1$-$C_4$ alkyl group, and
R represents a hydrogen atom or a $C_2$-$C_6$ acyl group;
with a heteroarylboronic acid or an alkyl heteroarylboronate starting compound of formula:

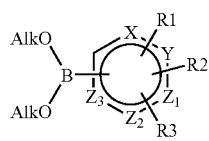

wherein:
X represents a nitrogen, oxygen or sulfur atom,
Y represents a carbon atom or a single bond,
Z₁, Z₂ and Z₃ each independently represent a carbon or nitrogen atom,
R₁, R₂ and R₃ each independently represent a hydrogen atom, a halogen atom, a cyano group, a $C_1$-$C_4$ alkyl group, a hydroxyl group, a $C_1$-$C_4$ alkoxy group, a trifluoromethyl group or a dialkylamino group; or
R₁ and R₂ together with the atoms of the heterocycle to which they are attached form an aromatic ring comprising 6 carbon atoms, whereby A represents a fused bicyclic group, and

64

Alk represents a hydrogen atom or a $C_1$-$C_4$ alkyl group; whereby the group:

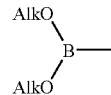

may also represent a pinacolatoboryl group,
in the presence of a palladium catalyst, of a polar solvent and of an inorganic base,
at a temperature of between 70° C. and 150° C. for 5 minutes to 72 hours,
to yield a compound of formula I:

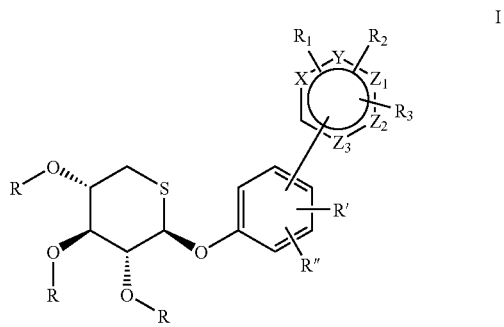

wherein R, R₁, R₂, R₃, R', R", X, Y, Z₁, Z₂ and Z₃ retain the same meanings as in the starting compounds;

b) optionally reacting the compound of formula I obtained above with a solution of ammonia in methanol to effect deacylation, whereby the acyl group is replaced by hydrogen atoms to yield a compound of formula Ia:

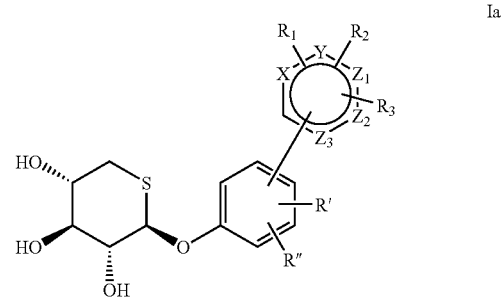

wherein R₁, R₂, R₃, R', R", X, Y, Z₁, Z₂ and Z₃ retain the same meanings as above; and c) optionally reacting one a compounds of formula I or Ia obtained above with an acid to yield the corresponding addition salt.

9. A process as claimed in claim 8, wherein Hal is bromine or iodine; R' and R" each independently represent a halogen atom other than bromine or iodine; A represents a benzothiazolyl, benzofuranyl, indolyl or benzothienyl group; said inorganic base is cesium fluoride or sodium carbonate; and the reacting step a) is performed in the presence of added lithium chloride.

10. A pharmaceutical composition comprising a compound as claimed in claim 1, and at least one pharmaceutically acceptable carrier or auxiliary.

11. A method of treating a condition selected from the group consisting of thrombosis, restenosis subsequent to an angioplasty and thromboembolytic pathologies in a subject, said method comprising administering to said subject a pharmacologically effective amount of a compound as claimed in claim 1.

12. A method as claimed in claim 11, wherein said condition is venous thrombosis or restenosis subsequent to an angioplasty.

* * * * *